US012788876B2

(12) United States Patent
McCullough et al.

(10) Patent No.: US 12,788,876 B2
(45) Date of Patent: *Nov. 10, 2026

(54) INSERTION MECHANISM FOR DRUG DELIVERY DEVICE

(71) Applicant: AMGEN INC., Thousand Oaks, CA (US)

(72) Inventors: Adam B. McCullough, Westlake Village, CA (US); Erich Coiner, Poway, CA (US); Alan D. Payne, Escondido, CA (US)

(73) Assignee: AMGEN INC., Thousand Oaks, CA (US)

( * ) Notice: Subject to any disclaimer, the term of this patent is extended or adjusted under 35 U.S.C. 154(b) by 353 days.

This patent is subject to a terminal disclaimer.

(21) Appl. No.: 18/642,384

(22) Filed: Apr. 22, 2024

(65) Prior Publication Data

US 2024/0382673 A1 Nov. 21, 2024

Related U.S. Application Data

(63) Continuation of application No. 16/489,833, filed as application No. PCT/US2018/021651 on Mar. 9, 2018, now Pat. No. 11,986,624.

(Continued)

(51) Int. Cl.
*A61M 5/142* (2006.01)

(52) U.S. Cl.
CPC .................. *A61M 5/14248* (2013.01); *A61M 2005/14252* (2013.01)

(58) Field of Classification Search
CPC .... A61M 5/14248; A61M 2005/14252; A61M 2005/14256; A61M 2005/1585;

(Continued)

(56) References Cited

U.S. PATENT DOCUMENTS 10,046,111 B2 8/2018 Schabbach et al.
11,464,900 B2 * 10/2022 McCullough ..... A61M 5/14248

(Continued)

FOREIGN PATENT DOCUMENTS

JP 2016530016 A 9/2016
WO WO-2005018703 A2 3/2005

(Continued)

OTHER PUBLICATIONS

International Search Report for International Application No. PCT/US2018/021651, dated Jun. 26, 2018.

(Continued)

*Primary Examiner* — Theodore J Stigell
(74) *Attorney, Agent, or Firm* — MARSHALL, GERSTEIN & BORUN LLP

(57) ABSTRACT

An insertion mechanism for a drug delivery device including a trocar, a housing, and a manifold in fluid communication with a fluid pathway connector and movable relative to the housing between a first manifold position adjacent to a proximal end of the housing and a second manifold position adjacent to a distal end of the housing. A hub carrying the trocar or hollow delivery needle is removably connected to the manifold, the hub being movable relative to the housing between a first hub position adjacent to the proximal end of the housing and a second hub position adjacent to the distal end of the housing. A power source is configured to generate rotational motion. A motion conversion mechanism operatively connects the power source and the hub, and is configured to convert the rotational motion into linear motion of the hub.

18 Claims, 13 Drawing Sheets

Related U.S. Application Data

(60) Provisional application No. 62/469,226, filed on Mar. 9, 2017.

(58) Field of Classification Search
CPC .... A61M 5/31576; A61M 2005/14208; A61M 2205/82; A61M 5/158; A61M 5/31571
See application file for complete search history.

(56) References Cited

U.S. PATENT DOCUMENTS

| | | | | | |
|---|---|---|---|---|---|
| 11,986,624 | B2 * | 5/2024 | McCullough | A61M 5/14248 | |
| 2013/0060233 | A1 * | 3/2013 | O'Connor | A61M 5/14248 | 604/151 |
| 2014/0276563 | A1 * | 9/2014 | Cole | A61M 5/158 | 604/164.01 |
| 2015/0306307 | A1 * | 10/2015 | Cole | A61M 5/14248 | 604/508 |
| 2016/0213837 | A1 * | 7/2016 | Schabbach | A61M 5/14244 | |

FOREIGN PATENT DOCUMENTS

| | | | |
|---|---|---|---|
| WO | WO-2008/024810 | A2 | 2/2008 |
| WO | WO-2015/164645 | A1 | 10/2015 |

OTHER PUBLICATIONS

Written Opinion for International Application No. PCT/US2018/021651, dated Jun. 26, 2018.
Japanese Patent Application No. 2019-548661, Notice of Rejection, mailed Aug. 17, 2021.
Final Office Action, U.S. Appl. No. 16/489,833, mailed Apr. 11, 2022.
Non-final Office Action, U.S. Appl. No. 16/489,833, mailed Sep. 29, 2021.
Advisory Action, U.S. Appl. No. 16/489,833, mailed Jul. 7, 2022.
Examiner's Answer to Appeal Brief, U.S. Appl. No. 16/489,833 mailed Mar. 17, 2023.
Decision on Appeal, U.S. Appl. No. 16/489,833, mailed Nov. 1, 2023.

* cited by examiner

INSERTION MECHANISM FOR DRUG DELIVERY DEVICE

CROSS-REFERENCE TO RELATED APPLICATIONS

This is a continuation of U.S. patent application Ser. No. 16/489,833, filed Aug. 29, 2019, which is the U.S. National Stage of PCT/US18/21651, filed Mar. 9, 2018, which claims the benefit of priority of U.S. Provisional Application No. 62/469,226, filed Mar. 9, 2017. The entire contents of each of the foregoing are incorporated herein by reference.

FIELD OF THE DISCLOSURE

The present disclosure generally relates to drug delivery devices, and more particularly, mechanisms and methods for inserting a trocar or hollow delivery needle of a drug delivery device into a patient so that a volume of a drug stored in the drug delivery device can be delivered to the patient.

BACKGROUND

Some drug delivery devices, such as on-body injectors, may be temporarily attached to a patient to deliver a drug via an injection needle or some other means over an extended period of time. The drug delivery device may be attached to the tissue of the patient's abdomen, thigh, arm, or some other portion of the patient's body.

In some cases, the drug delivery device may be worn by the patient for several minutes or hours while the drug is injected. For example, viscous drugs, including some biologics, can have long injection times due to the force needed to expel them from the drug delivery device. Furthermore, some drug delivery devices are configured to be attached to the patient at a doctor's office, and then later deliver the drug to the patient when the patient returns to his or her home. For these reasons and others, a rigid injection member may be left inside the patient for a substantial amount of time, which can result in patient discomfort or unease.

To address this issue, some drug delivery devices incorporate a cannula made of a flexible material for delivering the drug to the patient. Such a cannula can bend to adjust to the patient's body movements and therefore may be more comfortable than a rigid needle. However, due to its flexibility, the cannula may have difficulty penetrating the patient's skin during insertion. Therefore, an introducer needle or trocar is sometimes used to initially penetrate the skin and create a passageway for the cannula. The trocar may be subsequently retracted, leaving the cannula partially inside the patient's body.

The insertion and/or retraction movements of the trocar and/or cannula may be accomplished by incorporating an insertion mechanism disposed within the drug delivery device. Such an insertion mechanism, however, may increase the overall size, complexity, and/or cost of the drug delivery device.

The present disclosure sets forth insertion mechanisms and related methods embodying advantageous alternatives to existing insertion mechanisms and methods that may address one or more of the challenges or needs described herein, as well as provide other benefits and advantages.

SUMMARY

In accordance with a first aspect, a wearable drug delivery device may include a main housing, a container disposed in the main housing, an insertion mechanism disposed in the main housing, a fluid pathway connector defining a sterile fluid flowpath between the container and the insertion mechanism. The insertion mechanism may include a trocar or hollow delivery needle, an insertion mechanism housing having a proximal end and a distal end. Further, the insertion mechanism may include a manifold in fluid communication with the fluid pathway connector and movable relative to the insertion mechanism housing between a first manifold position adjacent to the proximal end of the insertion mechanism housing and a second manifold position adjacent to the distal end of the insertion mechanism housing. A hub carrying the trocar or hollow delivery needle may be removably connected to the manifold, the hub being movable relative to the insertion mechanism housing between a first hub position adjacent to the proximal end of the insertion mechanism housing and a second hub position adjacent to the distal end of the insertion mechanism housing. Further, a power source may be configured to generate rotational motion, and a motion conversion mechanism may be operatively connecting the power source and the hub, and configured to convert the rotational motion of the power source into linear motion of the hub.

In accordance with a second aspect, an insertion mechanism may include a trocar or hollow delivery needle, a housing having a proximal end and a distal end. Further, the insertion mechanism may include a manifold and movable relative to the housing between a first manifold position adjacent to the proximal end of the housing and a second manifold position adjacent to the distal end of the housing. A hub carrying the trocar or hollow delivery needle may be removably connected to the manifold, the hub being movable relative to the housing between a first hub position adjacent to the proximal end of the insertion mechanism housing and a second hub position adjacent to the distal end of the housing. Further, a power source may be configured to generate rotational motion, and a motion conversion mechanism may be operatively connecting the power source and the hub, and configured to convert the rotational motion of the power source into linear motion of the hub.

In accordance with a third aspect, a method may include providing a wearable drug delivery device comprising a container, a drug disposed in the container, an insertion mechanism, and a fluid pathway connector defining a sterile fluid flow path between the container and the insertion mechanism, the insertion mechanism having an insertion mechanism housing, a hub, a trocar or hollow delivery needle secured to the hub, a manifold in fluid communication with the fluid pathway and carried by the hub, a power source configured to generate rotational motion, a motion conversion mechanism having a rotating member operatively connecting the power source and the hub, and configured to convert the rotational motion of the power source into linear motion of the hub. Next, the method may include disposing the wearable drug delivery device in contact with a patient's skin and activating the power source to linearly move the hub, trocar or hollow delivery needle, and manifold in a distal direction so that the trocar or hollow delivery needle penetrates the patient's skin. Following, the method includes retracting the trocar or hollow delivery needle from the patient by moving the hub in the proximal direction. The method may include expelling the drug from the container, through the fluid pathway connector for subcutaneous delivery to the patient.

In further accordance with any one or more of the foregoing first and second aspects and methods, the insertion mechanism for a drug delivery device and method may include any one or more of the following forms or method steps.

In one form, the insertion mechanism may include a cannula having a hollow interior and being axially aligned with the trocar or hollow delivery needle. The manifold may be configured to fluidly connect the hollow interior of the cannula and the fluid pathway connector.

In one form, the motion conversion mechanism may include a pin and a yoke, the pin being slidably received in a slot formed in the yoke.

In one form, the pin may be operatively connected to and receiving rotational motion from the power source. Rotation of the pin in a first rotational direction over a first arc may cause the yoke to move linearly in a distal direction, and rotation of the pin in the first rotational direction over a second arc may cause the yoke to move linearly in a proximal direction.

In one form, the yoke may be rigidly connected to or integrally formed with the hub such that the hub and yoke move together jointly.

In one form, the motion conversion mechanism may include a guide post extending through an aperture formed in the yoke, the yoke being movable relative to the guide post.

In one form, the motion conversion mechanism may include a rotatable member rotatable about a rotational axis by the power source. The pin may extend from the rotatable member at a position offset from the rotational axis.

In one form, the hub may have a first stroke in which the hub initially moves from the first hub position to the second hub position to extend the trocar or hollow needle from the insertion mechanism housing. The hub may further include a second stroke in which the hub subsequently moves from the second hub position to the first hub position to retract the trocar or hollow needle into the insertion mechanism housing.

In one form, the hub may carry the manifold from the first manifold position to the second manifold position during the first stroke.

In one form, the insertion mechanism may include a catch member connected to the insertion mechanism housing and configured to engage a proximally facing surface of the manifold when the manifold occupies the second manifold position.

In one form, hub may be disconnected from the manifold by the catch member during the second stroke such that the catch member retains the manifold in the second manifold position while the hub returns to the first hub position.

In one form, the catch member may be configured to elastically deform to allow the manifold to move into the second manifold position during the first stroke.

In one form, the catch member may include a spring clip initially having an expanded configuration, the spring clip being compressed by the manifold during the first stroke and subsequently returning to the expanded configuration once the manifold reaches the second manifold position.

In one form, the insertion mechanism may include a lock member configured to selectively engage and prevent rotation of the rotatable member.

In one form, the rotatable member may have an outer surface including a circular portion and a non-circular portion, the lock member being configured to slide along the circular portion during rotation of the rotatable member and prevent further rotation of the rotatable member when the lock member engages the non-circular portion.

In one form of the method, activating the power source may include linearly moving a cannula secured to the manifold in the distal direction so that the trocar and cannula penetrate the patient's skin.

In one form of the method, retracting the trocar or hollow delivery needle may include disconnecting the hub from the manifold when the hub moves in the proximal direction to retract the trocar from the patient.

In one form of the method, expelling the drug may include expelling the drug from the container, through the fluid pathway connector, and into the cannula for subcutaneous delivery to the patient.

In one form, the method may include activating the motion conversion mechanism, the rotating member of the motion conversion mechanism including a yoke and the rotatable member including a pin, the pin being slidably received in a slot formed in the yoke.

In one form, the method may include rotating the rotatable member and the pin, the rotatable member operatively connecting the power source, wherein rotation of the rotatable member rotates the pin in a first rotational direction over a first arc causing the yoke to move linearly in the distal direction, and wherein rotation of the rotatable member rotates the pin in the first rotational direction over a second arc causing the yoke to move linearly in the proximal direction.

In one form, the method may include sliding the yoke by the motion conversion mechanism along a guide post, the guide post extending through an aperture formed in the yoke, the yoke being movable relative to the guide post.

In one form, activating the power source may include moving the hub during a first stroke from a first hub position adjacent to a proximal end of the insertion mechanism housing to a second hub position adjacent to a distal end of the insertion mechanism housing to extend the trocar or hollow needle from the insertion mechanism housing.

In one form of the method, retracting the trocar or hollow delivery needle may include moving the hub during a second stroke from the second hub position to the first hub position.

In one form, the method may include carrying the manifold by the hub during the first stroke from a first manifold position adjacent to the proximal end of the insertion mechanism housing to a second manifold position adjacent to the distal end of the insertion mechanism housing.

In one form of the method, engaging a proximally facing surface of the manifold by a catch member connected to the insertion mechanism housing when the manifold occupies the second manifold position.

In one form of the method, retracting the trocar or hollow delivery needle may include disconnecting the hub from the manifold by the catch member during the second stroke such that the catch member retains the manifold in the second manifold position while the hub returns to the first hub position.

In one form of the method, engaging a proximally facing surface of the manifold may include returning the catch member to an initial expanded configuration after first deforming as the manifold moves past the catch member in the distal direction.

In one form of the method, activating the power source may include releasing an energized torsion spring operatively coupled to the rotatable member of the motion conversion mechanism.

In one form, the method may include engaging a portion of the rotatable member with an obstructing edge to prevent the rotatable member from rotating.

In one form of the method, engaging the portion of the rotatable member may include rotating a lock member towards the rotatable member before the hub moves in the proximal direction, the lock member having the obstructing edge and being configured to selectively engage and prevent rotation of the rotatable member.

In one form of the method, engaging the portion of the rotatable member may include engaging a non-circular portion of the rotatable member with the insertion mechanism housing comprising the obstructing edge, the non-circular portion engaging the obstructing edge after the hub moves in the proximal direction.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings is necessarily to scale.

DETAILED DESCRIPTION OF THE DRAWINGS

Figure 1:
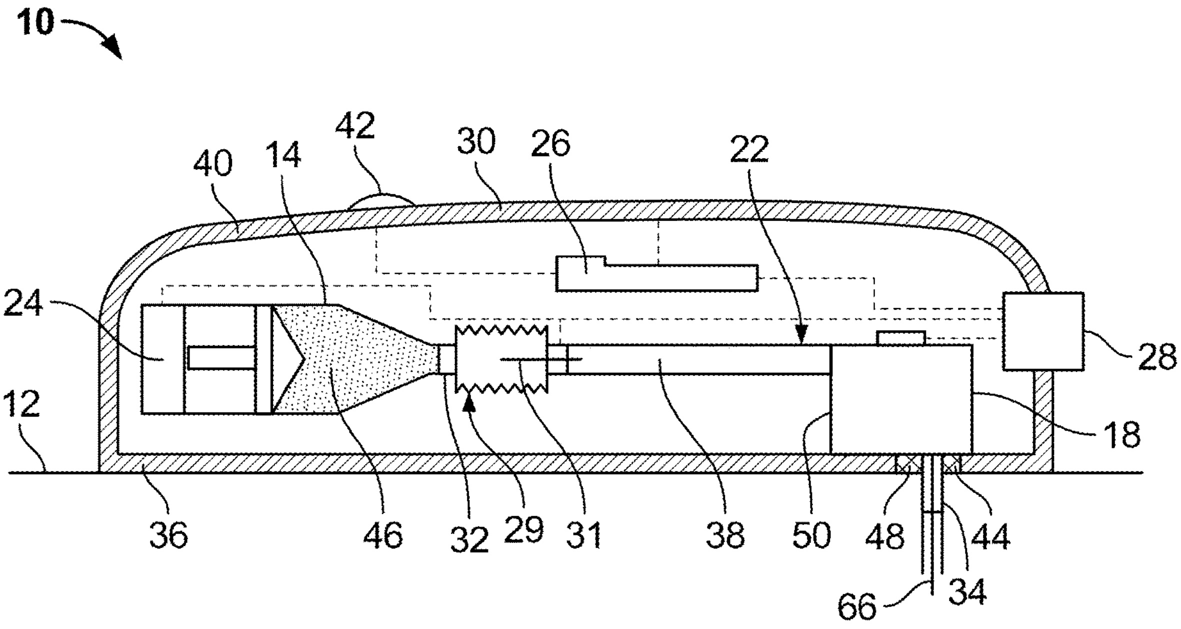
FIG. 1 is a schematic representation of one embodiment of a drug delivery device having an insertion mechanism in accordance with teachings of the present disclosure.

FIG. 1 illustrates one embodiment of a drug delivery device 10 according to the present disclosure. In at least one embodiment, the drug delivery device 10 may be configured as a wearable drug delivery device, such as an on-body injector, that may be attached to a patient's tissue 12 (e.g., the patient's skin) to administer delivery of a drug treatment. The drug delivery device 10 may automatically deliver a subcutaneous injection of a fixed or a patient/operator-settable dose of a drug over a controlled or selected period of time. The drug delivery device 10 may be intended for self-administration by the patient, but may also be used by a caregiver or a formally trained healthcare provider to administer an injection.

The drug delivery device 10 may include a container 14, an insertion mechanism 18, a fluid pathway connector 22, a drive mechanism 24, and a controller 26, each of which may be disposed in a main housing 30 of the drug delivery device 10. An actuator 28 (e.g., a depressible button) may be arranged on the exterior of the main housing 30 and configured to initiate operation of the drug delivery device 10 by activating the insertion mechanism 18, the drive mechanism 24, and/or the controller 26 via mechanical and/or electrical means (shown in dotted lines in FIG. 1). The fluid pathway connector 22 defines a sterile fluid flow path 38 between the container 14 and the insertion mechanism 18. The fluid pathway connector 22 may include a container access mechanism 29 configured to insert a container needle 31 through a septum 32 associated with the container 14 to establish fluid communication between the container 14 and the sterile fluid flow path 38 in response to activation of the drug delivery device 10, for example, via the actuator 28. The main housing 30 may include a bottom wall 36 to be releasably attached (e.g., adhered with an adhesive) to the patient's skin 12, and a top wall 40 including one or more indicator lights 42 and/or a window (not illustrated) for viewing the container 14. An opening 44 may be formed in the bottom wall 36, and optionally a septum 48 may extend across the opening 44 to seal the interior of the main housing 30 prior to use. The exterior of the insertion mechanism 18 may be defined by an insertion mechanism housing 50 separate from the main housing 30.

Upon activation of the drug delivery device 10, the insertion mechanism 18 may insert a cannula 34 and/or a trocar (or hollow delivery needle) 66 through the opening 44 and septum 48 and into the patient's tissue 12. Subsequently, the trocar 66 is removed from the patient's tissue 12 and retracts back into the insertion mechanism housing 50 while the cannula 34 remains deployed in the patient's tissue 12. Simultaneously or subsequently, the drug delivery device 10 may enable, connect, or open necessary connections to establish fluid communication between the container 14 and the fluid pathway connector 22. Next, the drive mechanism 24 may force a drug 46 stored in the container 14 through the sterile fluid flow path 38 of the fluid pathway connector 22 and into the cannula 34 for subcutaneous delivery to the patient.

FIGS. 2-7 illustrate an insertion mechanism 100 corresponding to one embodiment of the insertion mechanism 18 in FIG. 1. The insertion mechanism 100 may be incorporated in a drug delivery device such as the drug delivery device 10 depicted in FIG. 1. The insertion mechanism 100 includes an insertion mechanism housing 102, a trocar 106, and a cannula 110 having a hollow interior 112 which is axially aligned with and initially surrounding the trocar 106. Further, the insertion mechanism 100 includes a cannula guide 114 carrying the cannula 110 and a hub 116 carrying the trocar 106. The insertion mechanism 100 has a power source 118, a motion conversion mechanism 122 operatively connecting the power source 118 and the hub 116, and an activation member 170.

The function and operation of the insertion mechanism 100 will be described in three configurations: a pre-fired configuration shown in FIGS. 2 and 4 before the trocar 106 and cannula 110 are deployed; an inserted configuration shown in FIG. 5 where both the trocar 106 and cannula 110 extend through the housing 102 to establish a fluid pathway for drug delivery; and a retracted configuration shown in FIG. 6 where the trocar 106 is retracted back into the housing 102 and the cannula 110 remains extended through the housing and in position for drug delivery. In FIG. 7, the manifold 114 is in fluid communication with the fluid pathway connector 22, and is configured to fluidly connect the hollow interior 112 of the cannula 110 and the fluid pathway connector 22. The cannula guide 114 is movable relative to the housing 102 between a first cannula guide position adjacent to a proximal end 126 of the housing 102 shown in FIGS. 2 and 4, and a cannula guide manifold position adjacent to a distal end 130 of the housing 102 shown in FIGS. 5 and 6. The hub 116 is removably connected to the cannula guide 114 and is movable relative to the housing 102 between a first hub position adjacent to the proximal end 126 of the housing 102 shown in FIGS. 2, 4 and 6, and a second hub position adjacent to the distal end 130 of the housing 102 shown in FIG. 5. In this example, the cannula guide is a manifold 114.

In some embodiments, the trocar 106 may have a sharpened or beveled distal tip so that the trocar 106 is capable of piercing the patient's tissue 12 and introducing the cannula 110 inside the patient. The trocar 106 may also be referred to as an introducer needle. In some embodiments, the trocar 106 may be solid and thus does not have a hollow center. To facilitate this introducing functionality, the trocar 106 may be made of a more rigid material than the cannula 110. In some embodiments, the trocar 106 may be made of metal, whereas the cannula 110 may be made of plastic. Moreover, the relative flexibility of the cannula 110 may render the cannula 110 suitable for being left inside the patient for several minutes, hours, or days without substantial discomfort to the patient. In other embodiments, the trocar 106 and cannula 110 may either be replaced with a hollow delivery needle or just the trocar 106 may be replaced with a hollow delivery needle disposed within the hollow cannula 110.

Figure 2:
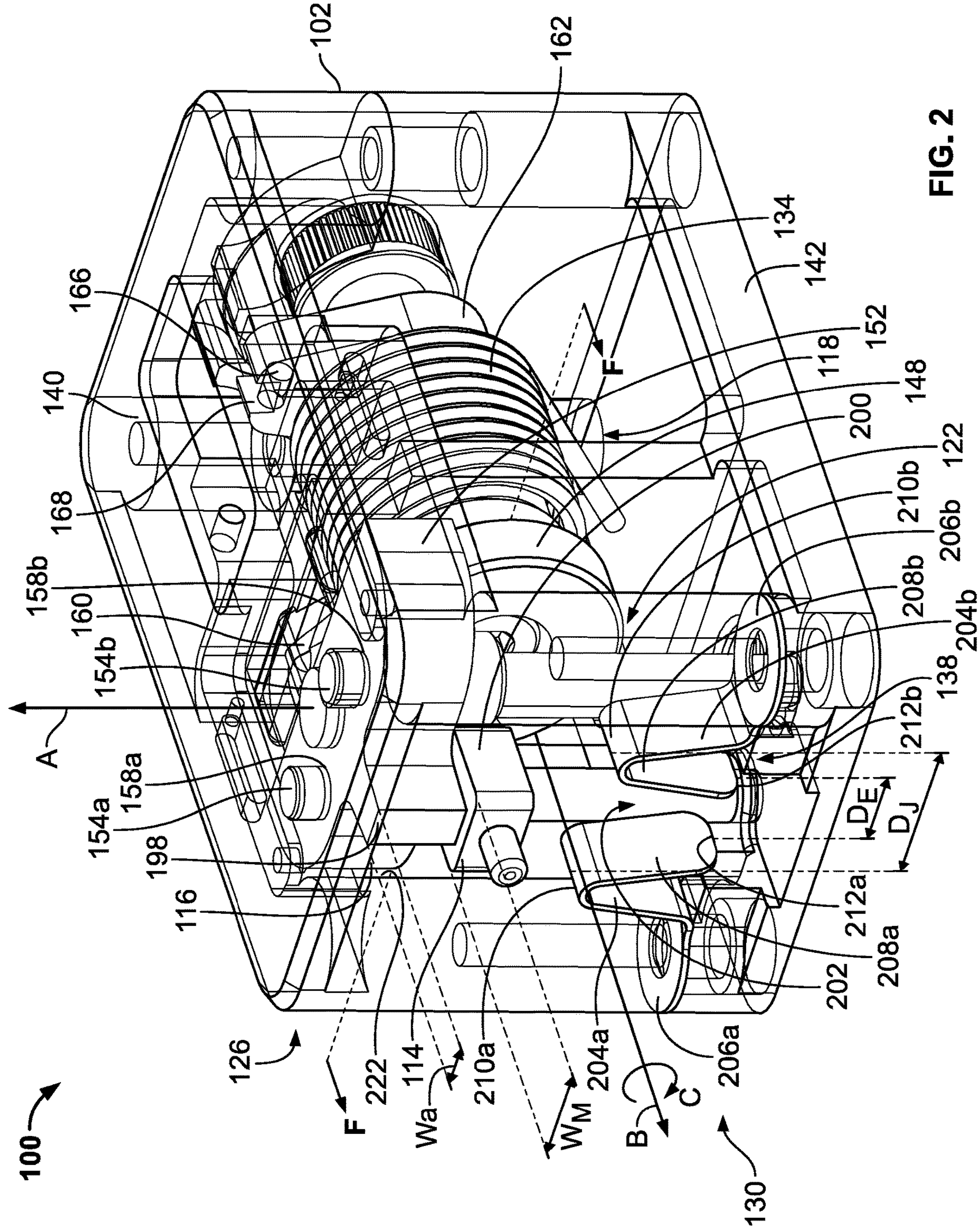
FIG. 2 is a perspective view of one embodiment of an insertion mechanism in a pre-fired configuration assembled in accordance with teachings of the present disclosure.
Figure 3:
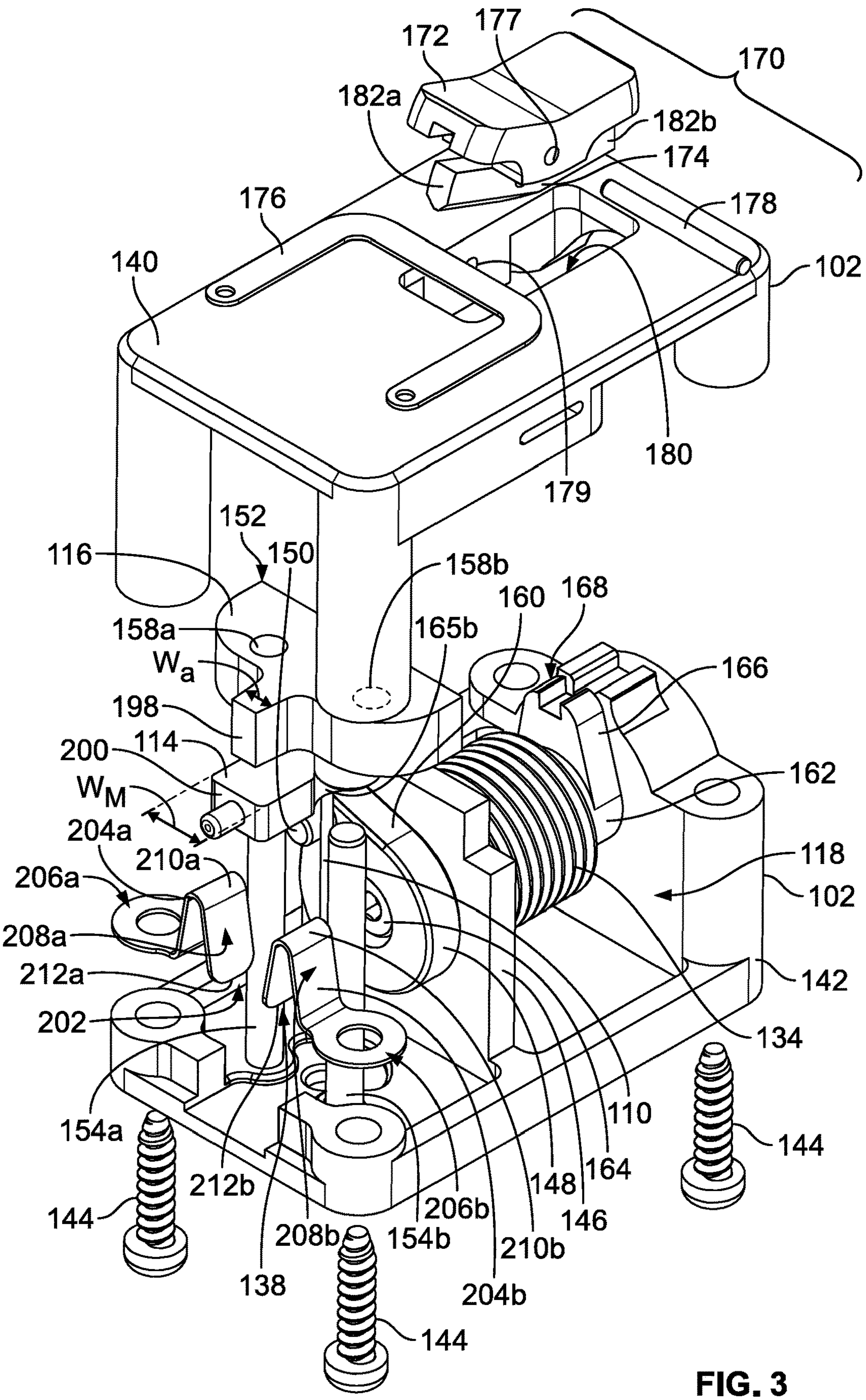
FIG. 3 is an exploded perspective view of the insertion mechanism of FIG. 2.

As shown in FIGS. 2 and 3, the power source 118 of the insertion mechanism 100 may include a torsion spring 134 and the motion conversion mechanism 122 may be a scotch yoke mechanism operatively coupled to the power source 118. The motion conversion mechanism 122 is configured to convert the rotational motion of the power source 118 into reciprocating linear motion of the hub 116 and manifold 114 to insert the trocar 106 and cannula 110 into the patient's tissue 12. Without added obstruction or interference to the power source 118, the motion conversion mechanism 122 is capable of continuing to retract the trocar 106 from the patient's tissue 12 by moving the hub 116 from the second hub position to the first hub position before completing a full 360 degree rotation. A catch member 138 attached to the housing 102 deforms to permit the manifold 114 to move from the first manifold position (i.e. the first cannula guide position) to the second manifold position (i.e. the second cannula guide position). When the manifold 114 occupies the second manifold position, the catch member 138 returns to its initial shape to engage the manifold 114 and maintain the cannula 110 deployed while the trocar 106 is retracted into the housing 102. In a single smooth rotation of a pin 150 of the motion conversion mechanism 122, the insertion mechanism 100 may insert both the trocar 106 and the cannula 110 to establish a drug delivery path and then automatically retract the trocar 106 without an additional step performed by the patient or healthcare provider. The smooth rotation of the scotch yoke mechanism 122, as will be described in detail below, may provide a smooth and comfortable insertion method for the patient, leaving only a flexible cannula inserted for drug delivery.

In FIGS. 2 and 3, the motion conversion mechanism 122 and power source 118 are enclosed within the housing 102 of the insertion mechanism 100 and between a cover 140 and a base 142. The power source 118 and the motion conversion mechanism 122 may be assembled first to the base 142 of the housing 102 before attaching the cover 140 to the base 142 to enclose the systems from the rest of the drug delivery device. In this embodiment, the cover 140 and the base 142 of the housing 102 are manufactured separately and then secured together by a plurality of fasteners 144 at each corner of the housing 102. The activation member 170 is operatively connected to the cover 140 such that the activation member 170 is externally accessible from the housing 102, and is configured to engage the power source 118 within the housing 102 in the pre-fired configuration. The base 142 includes a partition wall 146 which separates the motion conversion mechanism 122 and the power source 118 into different housing compartments. The partition wall 146 provides a support structure to facilitate assembly and operative connection between the motion conversion mechanism 122 and the power source 118. The power source 118 is operatively connected to the motion conversion mechanism 122 through the partition wall 146, which supports coaxial alignment of the power source 118 and the motion conversion mechanism 122 about the rotational axis B. Additionally, the separate compartments formed by the partition wall 146 permit the power source 118 and the motion conversion mechanism 122 systems to operate together without interfering with the adjacent system. In case of a sudden movement of the insertion mechanism 100 within the drug delivery device, or in case of component failure, moving parts of each system are held within their respective compartments and cannot enter the adjacent compartment and cause further disruption and/or failure. Moreover, assembling the cover 140 after the different components are attached to the base 142 is simple, reducing costs associated with complex assembly. In other embodiments, the housing 102 may be an integrated component without a separate base and cover components.

In a front compartment of the housing, the motion conversion mechanism 122 includes a rotatable member 148, a pin 150 extending from the rotatable member 148, a yoke 152, and first and second guide posts **154*a* and 154*b*. With a uniform speed of rotation of the pin 150 of the motion conversion member 122, a simple harmonic motion of the yoke 152 results, thereby providing a smooth insertion and retraction of the trocar 106. Although hidden in FIGS. 2 and 3, the yoke 152 includes a slot 186 to slidably receive the pin 150. The slot may be either a through-hole or a groove that stops short of extending all the way through the yoke 152. The pin 150 extends from a non-circular portion 160 of the rotatable member 148 at a position offset from a rotational axis B of the rotatable member 148. The yoke 152 includes first and second apertures 158***a* and 158*b* in which each respective guide post 154*a* and 154*b* extends therethrough. In the illustrated embodiment, the yoke 152 is rigidly connected to or integrally formed with the hub 116 such that the hub 116 and yoke 152 move together jointly as a single unit in the distal and proximal directions D and E along and parallel to the guide posts 154*a* and 154*b*.

Through the partition wall, the power source 118 and the rotatable member 148 are operatively connected. The pin 150 is also operatively connected to the power source 118 to receive rotational motion from the power source 118 via the rotatable member 148. The power source 118 includes a mandrel 162, which serves to support the rotatable member 148 within the housing 102, keep the rotatable member 148 aligned with the rotational axis B, transfer the rotational force of the torsion spring 134 to the motion conversion mechanism 122, and hold the torsion spring 134 in an energized state when the insertion mechanism 100 is in the pre-fired configuration. At one end, the mandrel 162 may be threadably connected to a central portion 164 of the rotatable member 148 by a fastener. At an opposing end, the mandrel 162 includes a flange 166 having a key slot 168 sized to receive the activation member 170. The mandrel 162 is operatively coupled to the torsion spring 134 such that the torsion spring 134 rotates the mandrel 162 when the mandrel 162 is released. In the pre-fired configuration, the flange 166 of the mandrel 162 is engaged with the activation member 170 to retain the torsion spring 134 in the energized state. After activation, the activation member 170 disengages from the flange 166 of the mandrel, causing the torsion spring 134 to rotate the mandrel 152, the pin 150, and the rotatable member 148 in direction C about the rotational axis B. The mandrel 162 and the torsion spring 134 may be provided in an energized package to reduce instances of spring release during assembly. Each end may be fastened to the base 142 of the housing 102 before the motion conversion mechanism 122 is provided. Once the cover 140 is attached to the base 142, the power source 118 may assume a ready configuration such that the activation member 170 can release the power source 118 when activated. In other embodiments, the power source 118 may be defined by a pressurized gas mechanism, an electric motor, an elastic membrane, a torsion spring, a leaf spring, and/or any other suitable mechanism for storing and releasing energy for rotating the components associated with the motion conversion mechanism 122.

Shown in FIG. 3, the activation member 170 includes a rocker 172, a key 174 sized to engage with the key slot 168 of the flange 166, a biasing member 176, and a pin 178. The pin 178 traverses through a bore 177 in the rocker 172, a bore in the key 174, and a bore 179 in the cover 140 to pivotably connect the rocker 172 and the key 174 to the cover 140. The activation member 170 is disposed within an aperture 180 formed in the cover 140 of the housing 102, and the biasing member 176 is disposed within the cover 140 with a portion extending into the aperture 180. When the insertion mechanism 100 is assembled, the activation member 170 is externally accessible from the housing 102 while configured to engage and activate the power source 118 disposed within the housing 102. In the pre-fired configuration, the biasing member 176 biases the rocker 172 to occupy a first rocker position in which a front portion 182*a* of the key 174 is moved away from the biasing member 176 and a back portion 182*b* of the key 174 is disposed through the aperture 180 of the cover 140 and disposed within the key slot 168 of the mandrel 166. To activate the activation member 170, the rocker 172 is pushed so that the rocker 172 and the key 174 pivots or rotates about the pin 178 such that the front portion 182*a* of the key 174 pushes against the biasing member 176 and the back portion 182*b* moves out of contact with the key slot 168 of the mandrel 162. Simultaneously or subsequently, the mandrel 162 is released and the torsion spring 134 applies a constant torsional load on the mandrel 162 and rotates the mandrel 162, the pin 150, and the rotatable member 148 about the rotational axis B. In some embodiments, the activation member 170 of the insertion mechanism 100 may be mechanically connected to actuator 28 of the drug delivery device 10 of FIG. 1 such that manual movement of the actuator 28 by a patient or healthcare provider may activate the insertion mechanism 100. In other embodiments, movement of the activation member 170 may be accomplished by an electromechanical feature operated by the controller 26 in response to movement of the actuator 28 by the patient or healthcare provider.

Operation of the insertion mechanism 100 will now be described with reference to the chronological sequence shown in FIGS. 4-6. In these figures, the rotatable member 148 is transparent and the power source 118 is hidden from view for clarity and to illustrate the movements of the insertion mechanism components. Turning first to FIG. 4, the motion conversion mechanism 122 of the insertion mechanism 100 is shown in the pre-fired configuration. The rotatable member 148 is disposed between the cover 140 and the base 142 of the housing 102 and is rotatable in a rotational direction C about the rotational axis B extending into the page. The rotatable member 148 has a non-circular portion 160 with a radius of curvature $R_1$ extending from the rotational axis B to a centerpoint of the pin 150, and a circular portion 188 with a radius of curvature $R_2$ extending from the rotational axis B to a circumferential surface 190 of the rotatable member 148. A pointed tip 185 of the non-circular portion 160 is in contact with an obstructing edge 194 protruding downward from the cover 140 of the housing 102 and disposed in a circumferential path 187 of the pointed tip 185. The pin 150 is disposed within a slot 186 formed in the yoke 152, where the slot 186 is defined by a groove extending in a direction perpendicular or otherwise non-parallel to a longitudinal axis A of the housing 102 from a first end 196*a* to a second end 196*b*. In some embodiments, the slot 186 may have a linear or substantially linear shape. The pin 150 extends from a position offset from, and in a direction parallel to, the rotational axis B, and is disposed on the non-circular portion 160 of the rotatable member 148. In the pre-fired configuration, the pin 150 is proximally located near the second end 196*b* of the slot 186 before moving closer to the second end 196*b* as it rotates in rotational direction C. As the rotatable member 148 rotates in direction C, the pin 150 rotates about rotational axis B along an outer circumferential path 151 defined by radius $R_1$, causing the yoke 152 to slide in the distal direction E.

Also shown in the pre-fired configuration, the hub 116 is in the first hub position at the proximal end 126 of the housing 102 and is disposed above the manifold 114 relative to the cover 140, the manifold 114 being in the first manifold position. The hub 116 and the manifold 114 may be removably connected when the hub 116 moves in the distal direction E, keeping the trocar 106 disposed within the hollow interior 112 of the cannula 110 until the hub 116 and the manifold 114 are in their respective second positions. The hub 116 and the manifold 114 may be connected or removably attached by friction, a bonding agent, adhesive, or other suitable mechanical attachment that keeps the manifold 114 connected to the hub 116 until the manifold 114 is disconnected from the hub 116 by the catch member 138. The yoke 152 includes two parallel apertures 158*a* and 158*b* sized to slidably receive first and second guide posts 154*a* and 154*b*, and the manifold 114 includes two arced edges 165*a* and 165*b* sized and shaped to fit around the guide posts 154*a* and 154*b*. During rotation of the rotatable member 148, the first and second guide posts 154*a* and 154*b* may constrain movement of the yoke 152 to a linear or substantially linear direction that is parallel or substantially parallel to the longitudinal axis A. Between the apertures 158*a* and 158*b* and behind the slot 186 of the yoke 152, the hub 116 includes a nose portion 198, which is depicted in FIGS. 2 and 3. The nose portion 198 is adjacent to, and may be removably attached from, a front portion 200 of the manifold 114. The nose portion 198 has a width $W_H$ and the front portion 200 has a width $W_M$ sized so that both the nose portion 198 and the front portion 200 can slide between a space 202 defined by the catch member 138. The front portion 200 of the manifold 114 is configured to receive the fluid conduit 22 of the drug delivery device 10 of FIG. 1.

Figure 4:
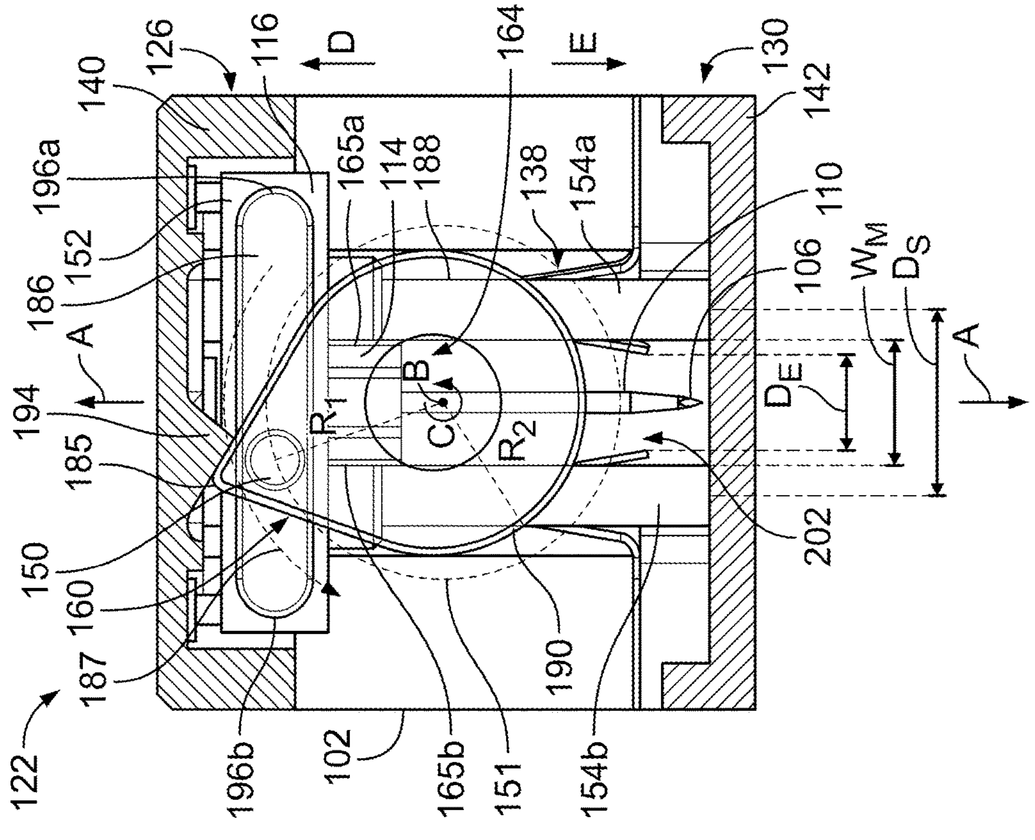
FIG. 4 illustrates a cross-sectional view of the insertion mechanism taken along line F-F of FIG. 2.

As shown in FIGS. 2, 3, and 4, the catch member 138 includes first and second spring clips 204*a* and 204*b* attached or otherwise secured to the housing 102 in the path of the manifold 114. So configured, each spring clip 204*a* and 204*b* deforms when the front portion 200 of the manifold 114 passes through the space 202 and subsequently elastically regains its original shape to lock the manifold 114 in the inserted configuration. Each spring clip 204*a* and 204*b* includes a holed flange 206*a* and 206*b* secured to the housing 102 and an arm 208*a* and 208*b* disposed within the housing 102 and expanded outwardly relative to the holed flange 206*a* and 206*b*. Each flange 206*a* and 206*b* receives one of the plurality of fasteners 144, and is secured between the cover 140 and the base 142 of the housing 102. Each arm 208*a* and 208*b* extends from their respective flange 206*a* and 206*b*, and is bent in a downward orientation at a joint 210*a* and 210*b*. Each arm 208*a* and 208*b* has a distal end 212*a* and 212*b* extending outwardly from the joint 210*a* and 210*b*, such that the distal ends 212*a* and 212*b* are inwardly disposed relative to the longitudinal axis A of the housing 102. The space 202 formed by the catch member 138 is defined by a distance between the joints DJ and the distance between the distal ends $D_E$ when the spring clip is in its expanded configuration. The catch member 138 elastically deforms such that the distance between the distal ends $D_E$ increases to be at least equal to the width $W_M$ of the front portion 200 of the manifold 114, thereby allowing the manifold 114 to move into the second manifold position. The catch member 138 returns to its original shape to engage a proximally facing surface 214 of the manifold 114 when the manifold 114 occupies the second manifold position. Because the width $W_H$ of the nose portion 198 of the hub is less than the distance $D_E$ when the catch member 138 is expanded, the nose portion 198 slides passed the catch member 138 when the hub 116 returns to the first hub position.

Figure 11:
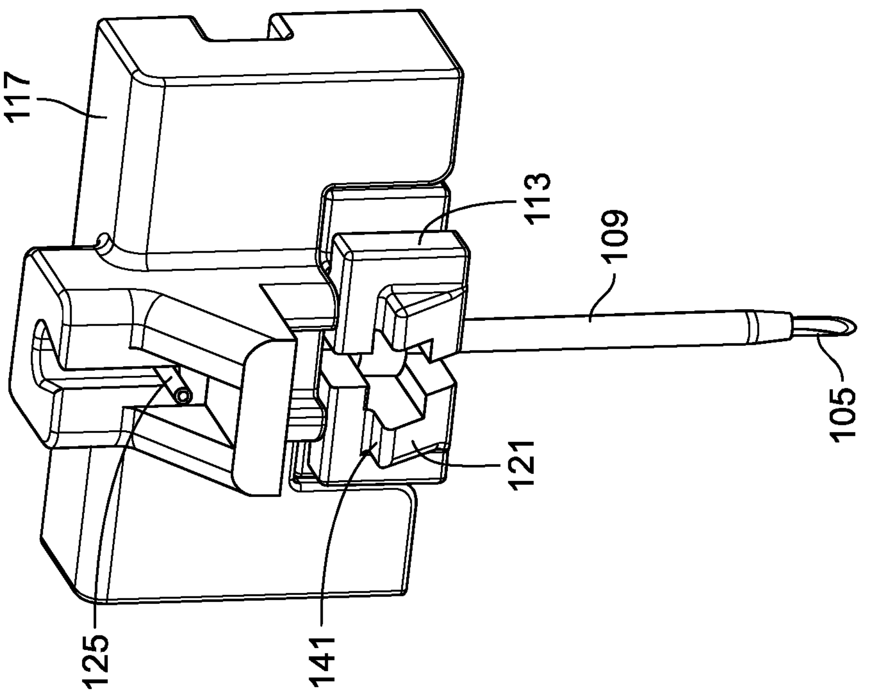
FIG. 11 illustrates a hub and cannula guide assembly of the insertion mechanism of FIG. 10.
Figure 10:
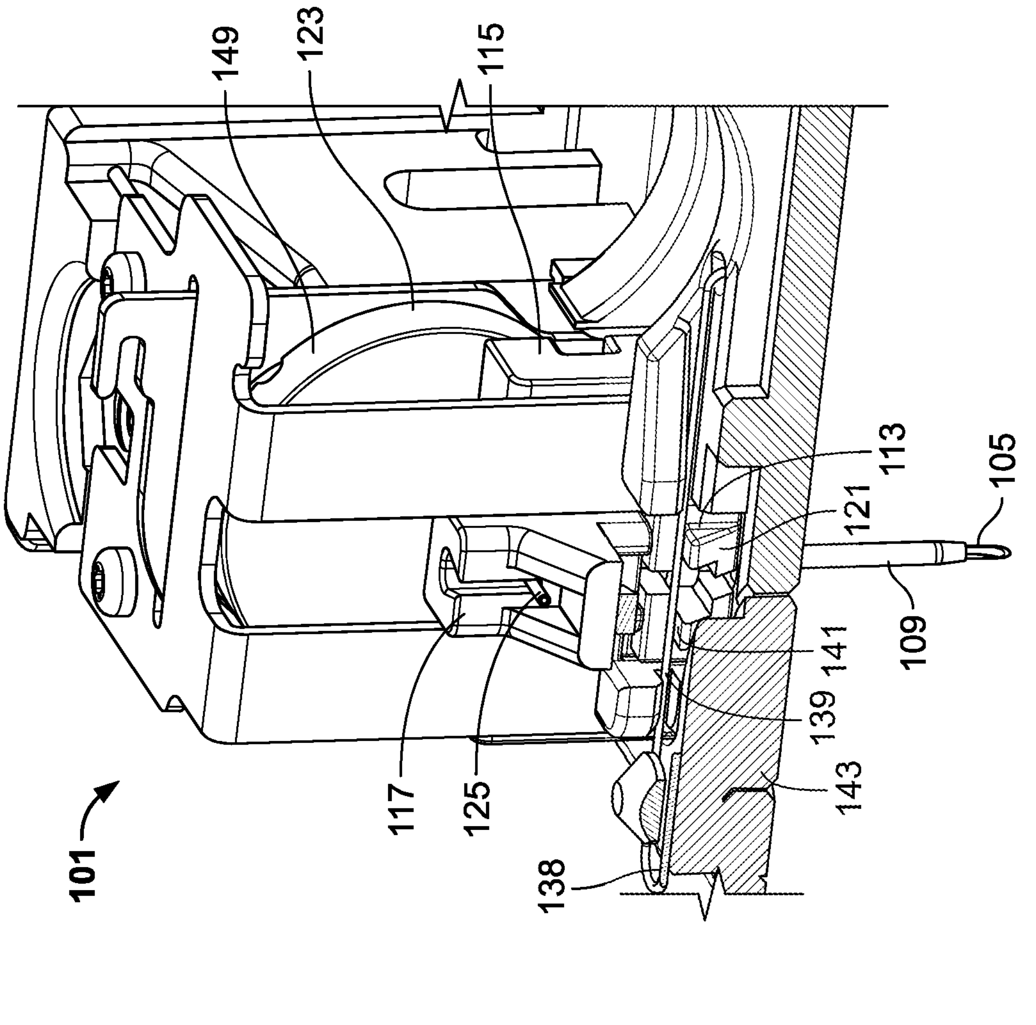
FIG. 10 illustrates a partial view of a second exemplary insertion mechanism constructed in accordance with the teachings of the present disclosure, the insertion mechanism in an inserted configuration.

In another example shown in FIGS. 10 and 11, a second exemplary insertion mechanism 101 may include a different catch member 138 that is configured to engage a cannula guide 113 when a hub 117 and the cannula guide 113 move to the inserted configuration. A motion conversion mechanism 123 includes a yoke 153 and a rotatable member 149, which causes the yoke 152, and therefore the hub 117 and cannula guide 113, to move linearly when the rotatable member 149 is rotated. The cannula guide 113, which may be similar to the manifold 114, carries the cannula 109 and the hub 117 carries a hollow delivery needle 105 to the inserted position for drug delivery. The cannula guide 113 and the cannula 109 remain in the second, or inserted, position as the hub 117 and the hollow delivery needle 105 return back to the first hub position. The catch member 138 includes a flexible clip 139 securely attached to a base 143 of the housing 103. As shown in FIG. 11, a shoulder 121 extending outwardly from the cannula guide 113 is arranged to deflect the clip 139 away from the cannula guide 113 as the cannula guide 113 moves to the inserted position. Once the cannula guide 113 is in the inserted configuration, the clip 139 snaps into a groove 141 formed in the shoulder 121 and locks the cannula guide 113 in place as shown in FIG. 10. As such, the clip 139 helps separate the cannula guide 113 from the hub 117, allowing the hub 117 and the hollow needle 105 to return to the initial hub position. In the retracted position, the hollow delivery needle 105 fluidly connects a fluid delivery path 125 to the cannula 109 to dispense the drug.

Figure 5:
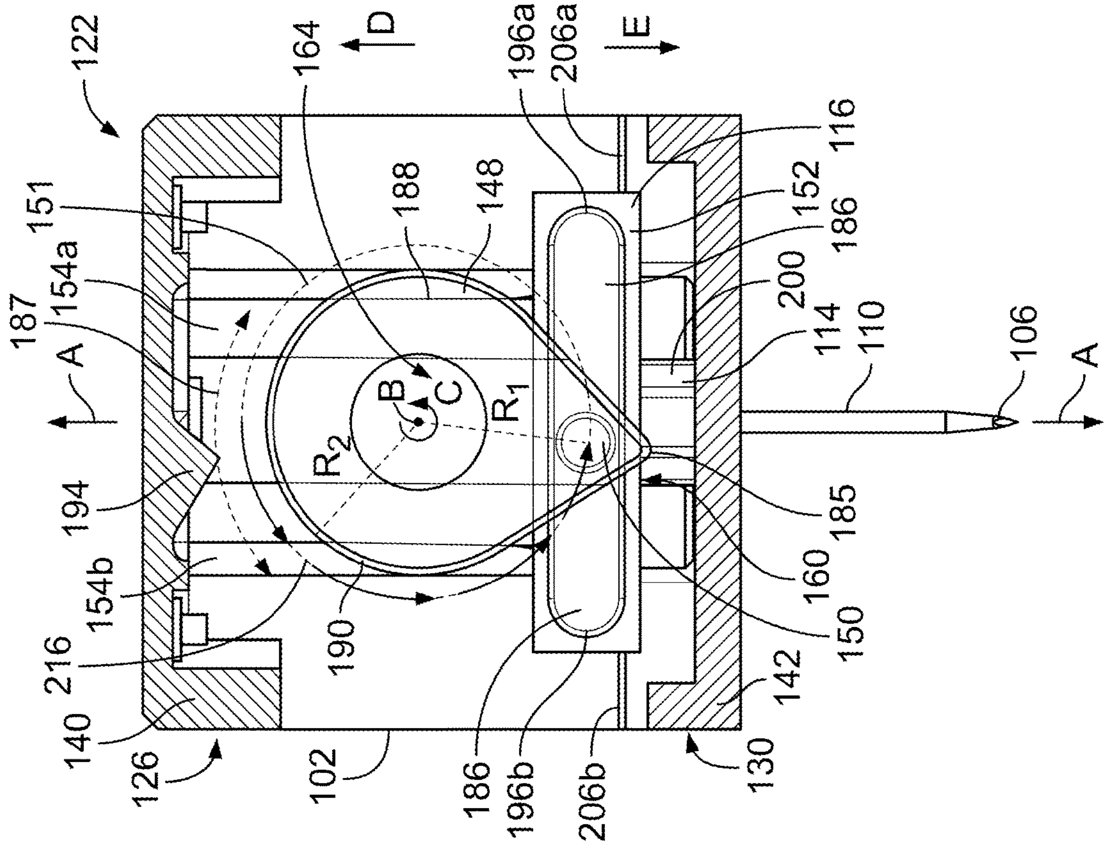
FIG. 5 illustrates the insertion mechanism of FIG. 4 in an inserted configuration.

Turning now to FIG. 5, the motion conversion mechanism 122 of the first exemplary insertion mechanism 100 is depicted in the inserted configuration. At the end of a first stroke of the hub 116, the hub 116 is in the second hub position and the manifold 114 is in the second manifold position. The first stroke may be defined as the travel path of the hub 116 between the pre-fired configuration and the inserted configuration of the insertion mechanism 100. Alternatively, the first stroke may be defined by the length of time from activation of the insertion mechanism 100 until the insertion mechanism 100 reaches the inserted configuration. During the first stroke, the hub 116 moves from the first hub position to the second hub position to extend the trocar 106 or hollow needle from the insertion mechanism housing 102. Concurrently, the hub 116 carries the manifold 114 in the distal direction E from the first manifold position to the second manifold position. During the first stroke, the manifold 114 compresses the arms 208*a* and 208*b* of the catch member 138 until the manifold 114 reaches the second manifold position, at which point the distal ends 212*a* and 212*b* of the catch member 138 return to the expanded configuration. The pin 150 rotates in a first rotational direction C from its initial position depicted in FIG. 4 to a position located near the base 142 of the housing 102. Following the circumferential path 151 of the pin 150, the pin 150 of the motion conversion mechanism 122 rotates over a first arc 216, causing the yoke 152 to move linearly in the distal direction E.

Figure 6:
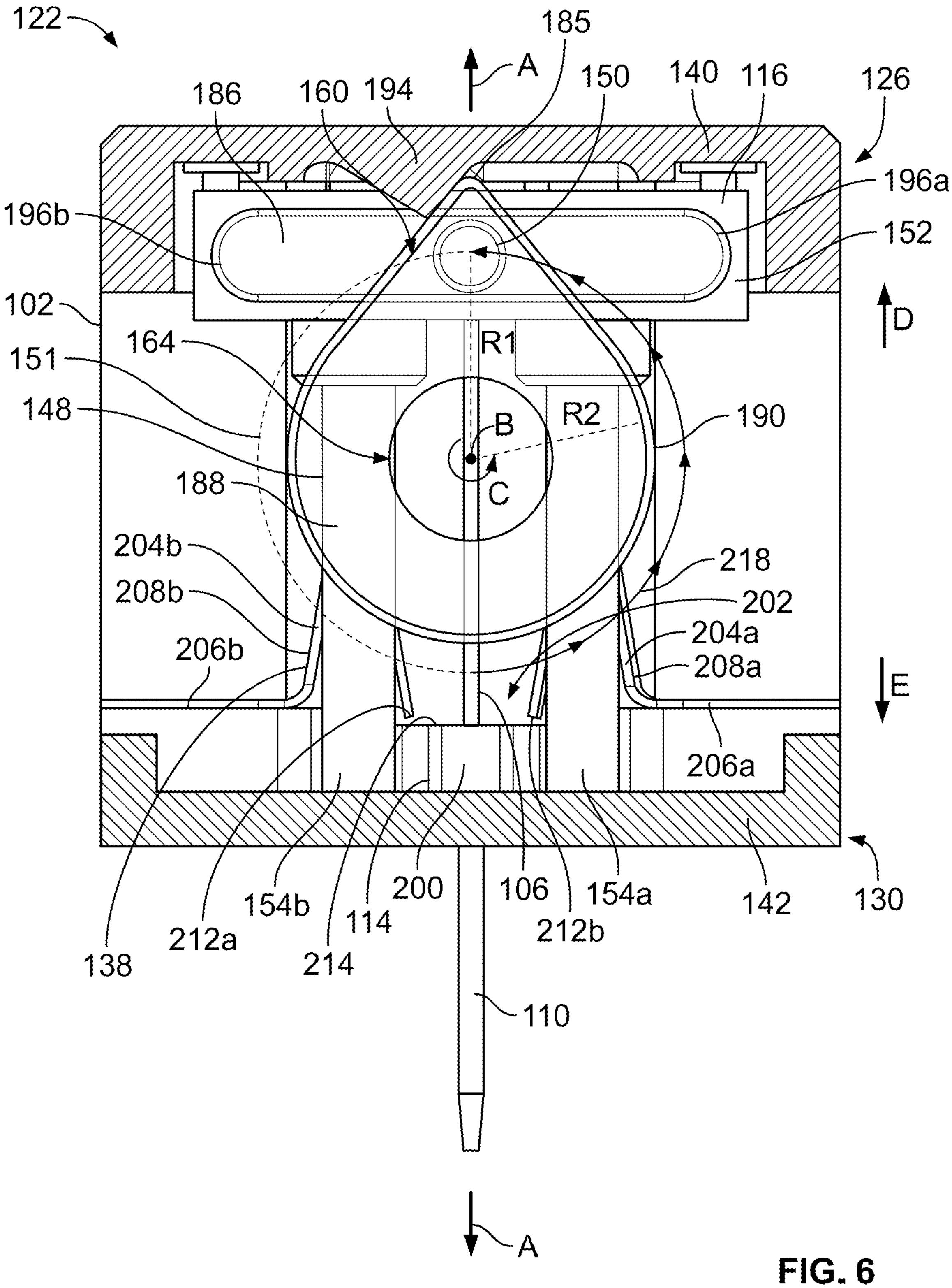
FIG. 6 illustrates the insertion mechanism of FIG. 4 in a retracted configuration.
Figure 7:
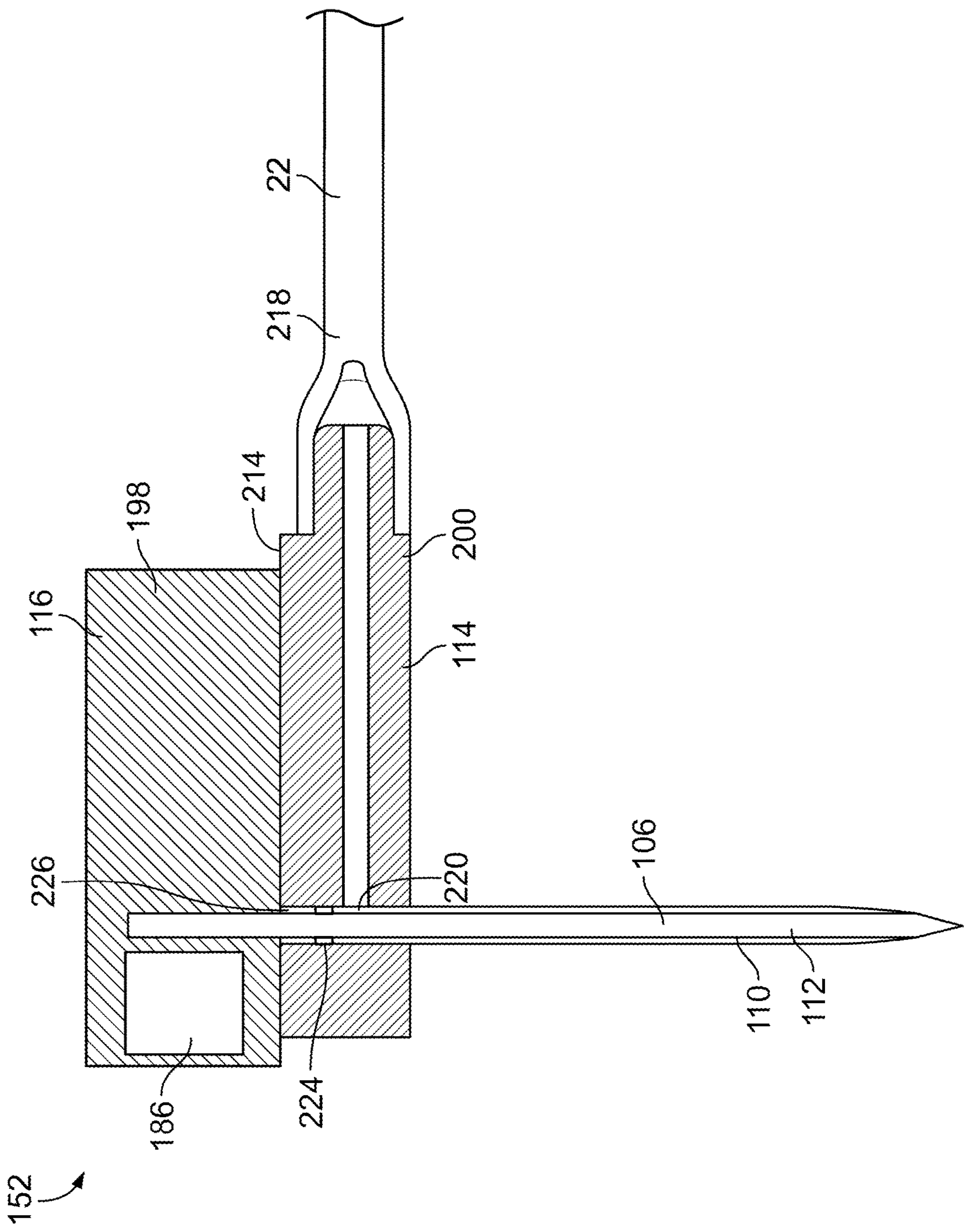
FIG. 7 illustrates a cross-sectional view of a hub, trocar, manifold, cannula, and a fluid pathway connector of the insertion mechanism of FIGS. 2-6.

In FIG. 6, the motion conversion mechanism 122 of the insertion mechanism 100 is in the retracted configuration. At the end of a second stroke, the hub 116 is in the first hub position and the manifold 114 remains in the second manifold position. The second stroke may be defined by the travel path of the hub 116 between the inserted configuration and the retracted configuration of the insertion mechanism 100. Alternatively, the second stroke may be defined by length of time from the end of the first stroke and until the insertion mechanism 100 reaches the retracted configuration. During the second stroke, the hub 116 moves from the second hub position to the first hub position to retract the trocar 106 or hollow needle into the insertion mechanism housing 102. Also during the second stroke, the catch member 138 disconnects the hub 116 from the manifold 114 and retains the manifold 114 in the second manifold position while the hub 116 returns to the first hub position. Depicted in FIG. 6, the distal ends 212*a* and 212*b* of the catch member 138 are disposed between the proximally facing surface 214 of the manifold 114. The pin 150 of the motion conversion mechanism 122 rotates in the first rotational direction C over a second arc 218 of the circumferential path 216, causing the yoke 152 to move linearly in the proximal direction D.

Shown in FIG. 7, the fluid pathway connector 22 and the cannula 110 are connected to the manifold 114 such that the cannula 110 and the fluid pathway connector 22 can move relative to the housing 102 when the insertion mechanism 100 is activated. The fluid pathway connector 22 includes a flexible fluid conduit 218 in fluid communication with an internal chamber 220 of the manifold 114. The flexible fluid conduit 218 may define a portion, or the entirety, of the sterile fluid flow path 38 depicted in FIG. 1. As shown in FIG. 2, a vertical channel or opening 222 defined by the cover 140 and the base 142 permits the fluid pathway connector 22 and flexible fluid conduit 218 to move relative to the housing 102 when the manifold 114 moves between the first manifold position and the second manifold position. The manifold 114 includes a septum 224 disposed in the internal chamber 220 of the manifold 114. The trocar 106 is disposed through the septum 224 when the insertion mechanism 100 is both in the pre-fired and inserted configurations. As the trocar 106 returns with the hub 116 to the first hub position, the trocar 106 moves in the proximal direction D relative to the housing 102, thereby passing through the internal chamber 220, the septum 224, and an opening 226 in the proximally facing surface 214 of the manifold 114. The septum 224 seals the opening 226 closed so that fluid cannot escape through the opening 226 during drug delivery. In some embodiments, the trocar 106 may retract from the internal chamber 220 when the manifold 114 and cannula 110 are arranged in the second manifold position so that the trocar 106 is isolated from the sterile fluid flow path 38 during drug delivery. In other embodiments, the insertion mechanism 100 may not include a cannula 110 and instead includes a hollow delivery needle in fluid communication with the fluid pathway connector 22 via the manifold 114. In this case, the hollow delivery needle is a rigid material capable of piercing a patient's tissue 12 that remains inside the patient until drug delivery is complete. As the hollow delivery needle acts as both an introducer and a drug delivery conduit for the insertion mechanism 100, the manifold and the hub may be integrally formed. In another embodiment, the insertion mechanism 100 may be more compact to permit the trocar 106 to retract into the septum 224, the opening 226, and be sufficiently removed from the internal chamber 220 to permit fluid flow.

Figure 12:
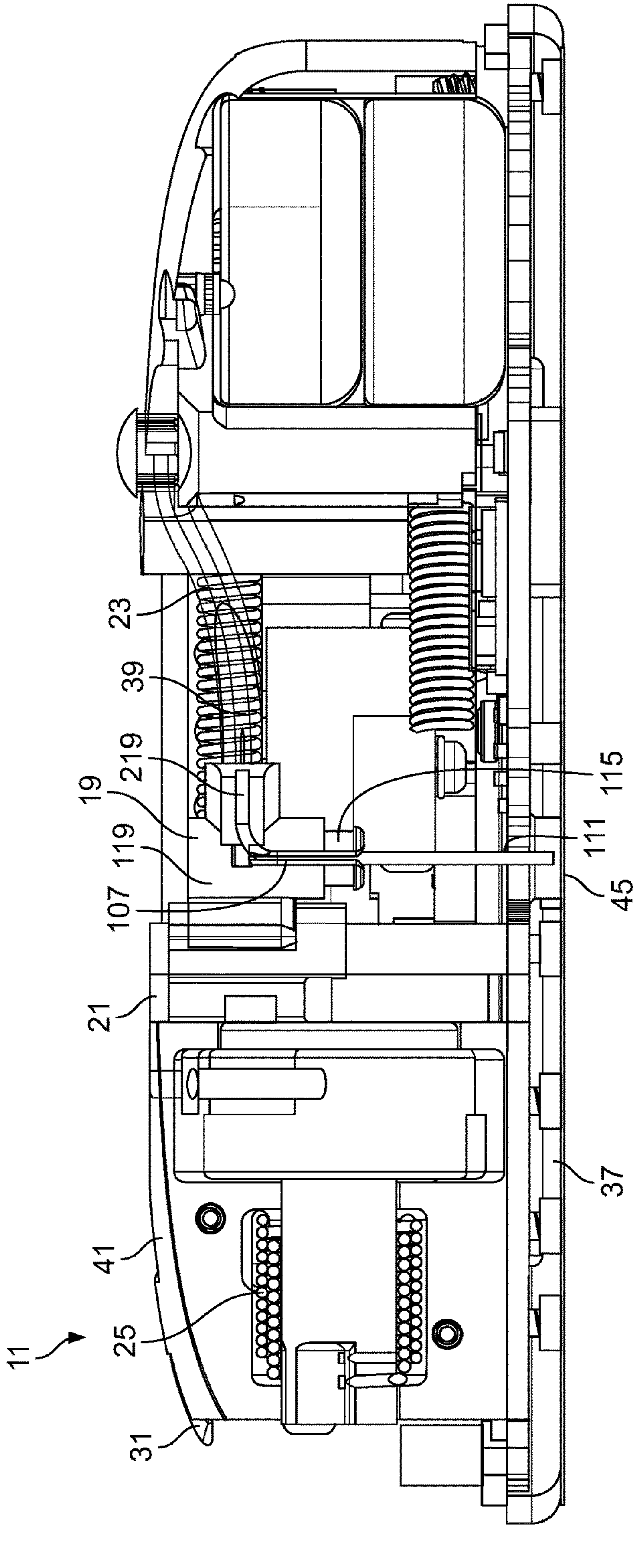
FIG. 12 illustrates a cross-sectional view of a second exemplary drug delivery device constructed in accordance with the teachings of the present disclosure.

In a second exemplary drug delivery device 11 shown in FIG. 12, a container holding a drug (not shown), a third exemplary insertion mechanism 19, a fluid pathway connector 23, a drive mechanism 25, and a controller are disposed in a main housing 31 of the drug delivery device 11. An actuator (e.g., a depressible button) may be arranged on the exterior of the main housing 31 and configured to initiate operation of the drug delivery device 11 by activating the insertion mechanism 19, the drive mechanism 25, and/or the controller via mechanical and/or electrical means. The fluid pathway connector 23 defines a sterile fluid flow path 39 between the container and the insertion mechanism 19. The fluid pathway connector 23 may include a container access mechanism (not illustrated) configured to insert a container needle through a septum associated with the container to establish fluid communication between the container and the sterile fluid flow path 39 in response to activation of the drug delivery device 11, for example, via the actuator. The main housing 31 may include a bottom wall 37 to be releasably attached (e.g., adhered with an adhesive) to the patient's skin, and a top wall 41 including one or more indicator lights and/or a window (not illustrated) for viewing the container. An opening 45 may be formed in the bottom wall 37. The insertion mechanism 19 includes a motion conversion mechanism 21 may be configured to operate similarly to the motion conversion mechanism 122 of the first exemplary insertion mechanism 100.

Figure 13:
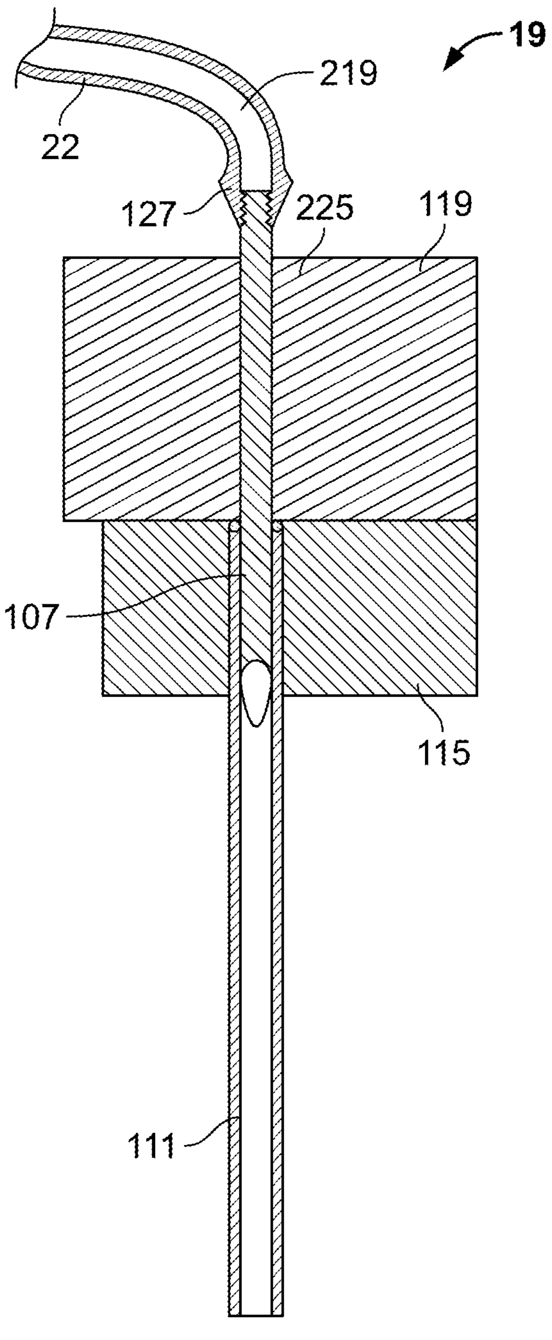
FIG. 13 illustrates a cross-sectional view of a hub, hollow need, cannula guide, cannula, and a fluid pathway connector of a third exemplary insertion mechanism of FIG. 12.

By comparison to the first exemplary insertion mechanism 100, the third exemplary insertion mechanism 19 of FIGS. 12 and 13 include a hollow needle 107 that is fluidly connected to the fluid pathway connector 23. In this case, the insertion mechanism 19 does not include a manifold 114 for fluid connection to a container containing a drug. Instead, a fluid path 219 is directly connected to a barbed end 127 of the hollow needle 107, as shown in FIG. 13, and the hollow needle 107 is configured to dispense a drug into a cannula 111 for drug delivery. In operation, a cannula guide 115, which may be similar to the manifold 114, carries the cannula 111 to the second position with a hub 119 for drug delivery, and remains in the second position when the hub 119 returns to the first hub position. When the hub 119 is retracted back to the first hub position, a drug may be expelled from the container, through the fluid pathway connector 23 and fluid path 219, into the hollow needle 107 and finally into the cannula 111 for delivery to a patient. A seal 225, such as an O-ring, is disposed around an outer diameter of the hollow needle 107 in the cannula guide 115 to provide a sealed pathway for fluid delivery. The cannula guide 115 may be removably connected to the hub 119, like the manifold 114, or the cannula guide 115 may be removably connected to the hub 119 by another mechanism.

Figure 8:
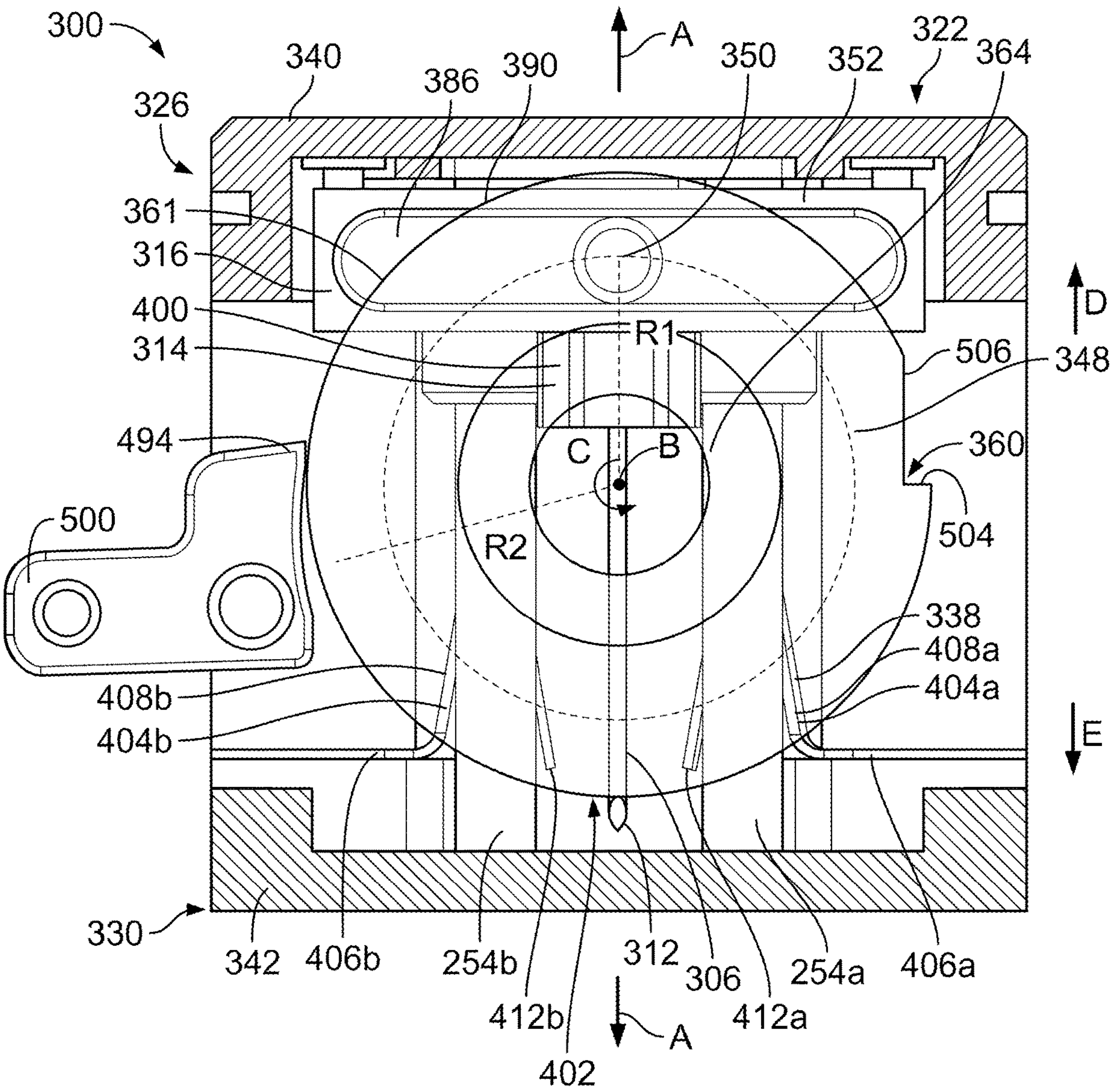
FIG. 8 illustrates a cross-sectional view of a fourth exemplary insertion mechanism constructed in accordance with the teachings of the present disclosure, the insertion mechanism in a pre-fired configuration.
Figure 9:
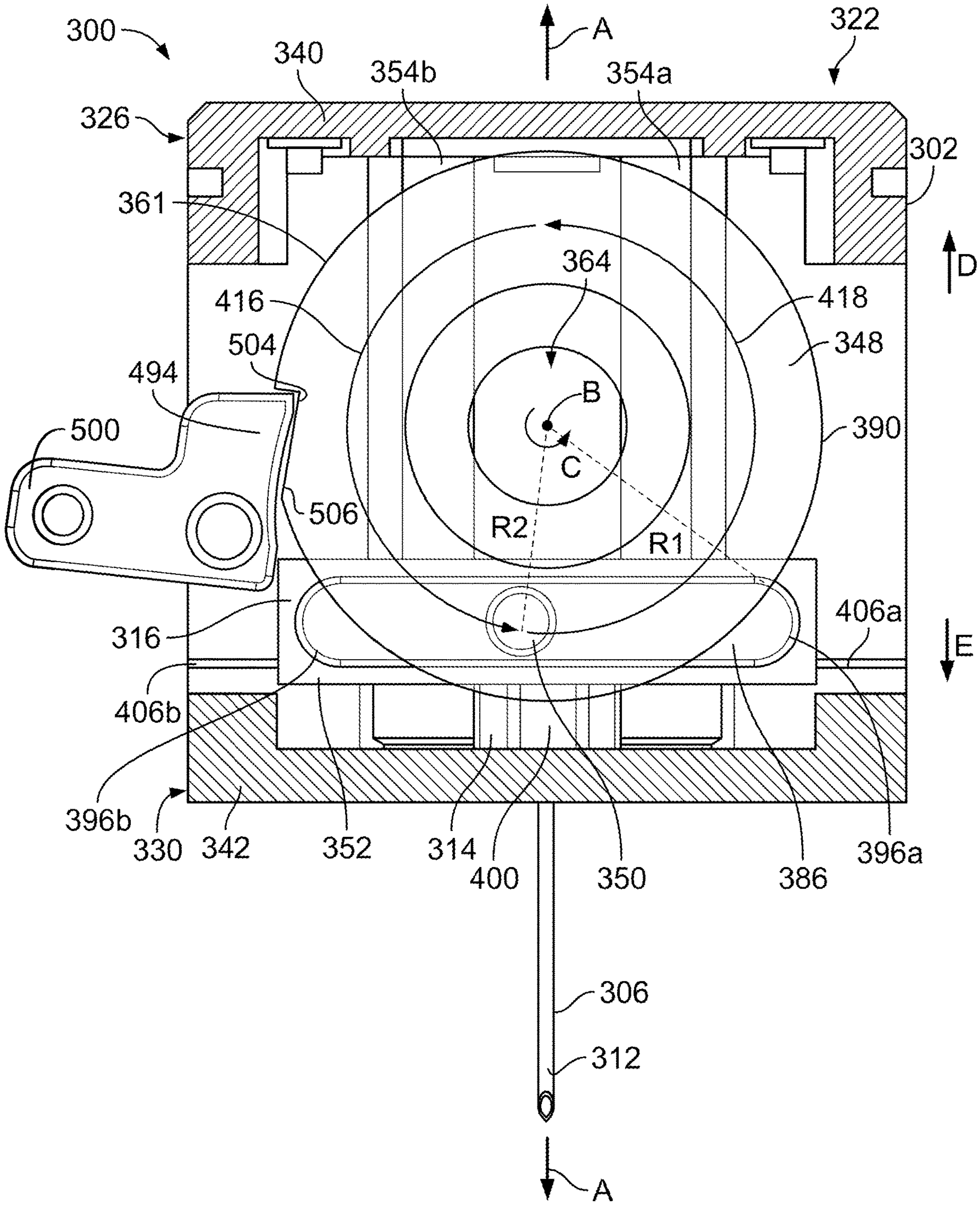
FIG. 9 illustrates the insertion mechanism of FIG. 8 in an inserted configuration.

In FIGS. 8 and 9, a fourth exemplary insertion mechanism 300 is illustrated in accordance with another embodiment of the present disclosure. The fourth exemplary insertion mechanism 300 is similar to the first exemplary insertion mechanism 100 described above, except for the configuration of the motion conversion mechanism 322. Additionally, the insertion mechanism 300 of the present embodiment does not have a cannula, but instead the introducer is a hollow delivery needle 306. Other elements of the insertion mechanism 300 in FIGS. 8 and 9 which are similar to the elements of the insertion mechanism 100 are designated by the same reference numeral, incremented by 200. A description of many of these elements is abbreviated or even eliminated in the interest of brevity. Further, the insertion mechanism 300 may be incorporated into a drug delivery device such as the drug delivery device 10 depicted in FIG. 1 or the drug delivery device 11 depicted in FIG. 12.

The insertion mechanism 300 is illustrated in FIGS. 8 and 9 from a similar perspective as the cross-sectional view F-F of the insertion mechanism 100 in FIG. 2. Here, the manifold 314 and the hub 316 are fixedly attached so that they may not disconnect when the hub 316 moves in the proximal direction D to retract the hollow delivery needle 306 during the second stroke. Rather, the hub 316 and the manifold 314 may be integrally formed with the yoke 352 so that the yoke 352, manifold 314, and hub 316 move together jointly as a single unit between the pre-fired, the inserted, and the retracted configurations. In the pre-fired configuration, the pin 350 is disposed within the slot 386 of the yoke 352 at the proximal end 326 of the housing 302. During the first stroke over the first arc 416 of the pin 350, the hub 316 carries the manifold 314 so that the manifold moves from the first manifold position in FIG. 8 to the second manifold position in FIG. 9. Similarly, the hub 316 and the yoke 352 slide in the distal direction E from the first hub position to the second hub position, inserting the hollow delivery needle 306 through the distal end 330 of the housing 302.

Simultaneously or subsequently, a spring-biased lock member 500 having an obstructing edge 494 engages with the non-circular portion 360 of the rotatable member 348. The non-circular portion 360 of this embodiment includes an angled indentation 506 forming an abrupt corner 504 in the circumferential surface 390 of the rotatable member 348. The angled indentation 506 is shaped to guide the obstructing edge 494 of the spring-biased lock member 500 into the corner 504 so that the obstructing edge 494 eventually stops the rotatable member 348 from rotating when the pin 350 moves over the first arc 416. As the pin 350 rotates in the circumferential path 351, the obstructing edge 494 of the spring-biased lock member 500 slides against the circumferential surface 390 of the circular-portion 388 of rotatable member 348. The spring-biased lock member 500 may be slightly biased in the proximal direction E so that it rotates inwardly toward the rotatable member 348 to make continuous contact with a circular portion 361 of the circumferential surface 390 during the first stroke. As the non-circular portion 360 of the rotatable member 348 contacts the obstructing edge 494, the lock member 500 moves inwardly toward the rotatable member 348 until the obstructing edge 494 catches the corner 504 preventing further rotation of the rotatable member 348. The first stroke may end once the obstructing edge 494 catches the corner 504 of the non-circular portion 360.

In the inserted configuration in FIG. 9, the pin 350 is at the distal end 330 of the housing after moving over the first arc 416. The manifold 314 may be in fluid communication with the fluid pathway connector 22, and is configured to fluidly connect the hollow interior 312 of the hollow delivery needle 306 and the fluid pathway connector 22. When the spring-biased lock member 500 has engaged the rotatable member 348, the container access mechanism 29 may be activated to being fluid delivery through the hollow delivery needle 306. When drug delivery is complete, the lock member 500 may be biased in the distal direction E to disengage the obstructing edge 494 from the corner 504 of the non-circular portion 360, permitting the pin 350 to continue rotation in the C direction over arc 418. After drug delivery is complete and during the second stroke, the pin 350 moves over the second arc 418 to retract the hollow delivery needle 306 into the housing 302. In another embodiment, the hub 316 and the manifold 314 may be disconnected when the hub 316 moves in the proximal direction D by the catch member 338. In this case, the power source 318 and the motion conversion mechanism 322 are configured to prevent the hub 316 carrying the hollow delivery needle 306 from moving back in the proximal direction E.

In the disclosed embodiments, the displacement of the yoke 152 and 352 is a function of the pin 150 and 350 position. That is, at maximum depth of the trocar 106 or hollow delivery needle 306, the pin is rotated to its lowest position. The torsion spring 134 and 334 may be provided such that it supplies a torque that is greater than or equal to the system torque for all positions of the pin 150 and 350, from 0-360 degrees. In a case where the pin 150 and 350 rotates 360 degrees, a torsion spring having a deflection angle of 360 degrees may be provided. To maintain spring torque in during the second stroke, the spring angular position will need to be offset with respect to the position of the pin 150 and 350. So configured, when the pin 150 and 350 reaches the final position at the 360 degrees mark, the spring 134 and 334 still supplies torque. In a preferred embodiment the angular start position of the pin is 20 degrees, the radius $R_1$ of the pin is 5.16 mm, the mass of the moving manifold 114 and hub 116 is 0.286 g, the torsion spring rate of the torsion spring 134 is 0.096 N-m/degree, and the max torque at 360 degrees is 34.7N-m to achieve a 0.01 s insertion time, 8 mm injection depth, and 25 mm device height.

Figure 16:
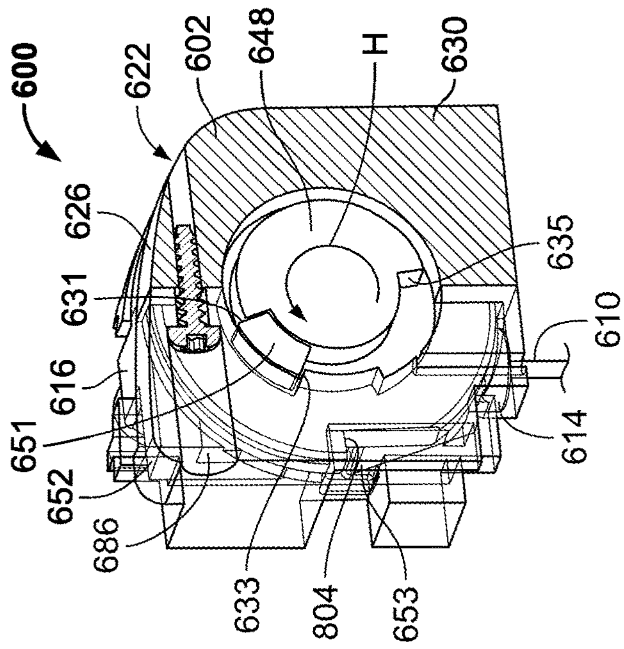
FIG. 16 illustrates the insertion mechanism of FIG. 14 in a retracted configuration.
Figure 15:
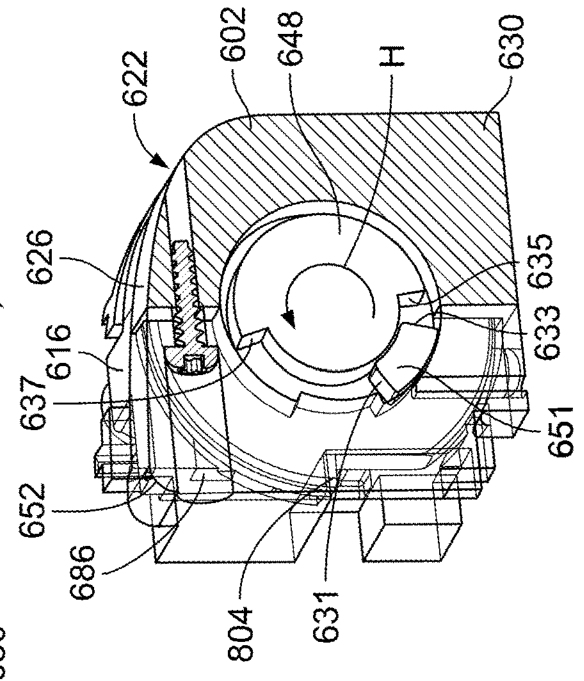
FIG. 15 illustrates the insertion mechanism of FIG. 14 in a loaded configuration.
Figure 14:
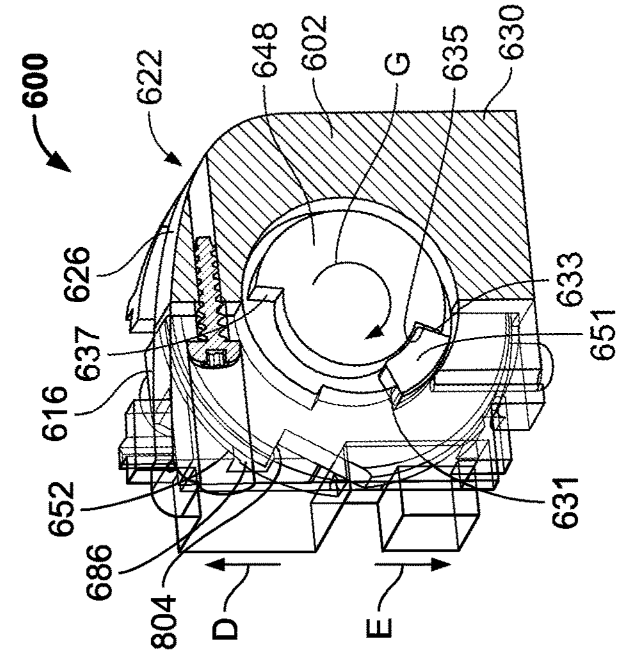
FIG. 14 illustrates a fifth exemplary insertion mechanism constructed in accordance with the teachings of the present disclosure, the insertion mechanism in a pre-loaded configuration.

In FIGS. 14-16, a fifth exemplary insertion mechanism 600 is constructed in accordance with the teachings of the present disclosure. The fifth exemplary insertion mechanism 600 is similar to the fourth exemplary insertion mechanism 300 described above, except for the operation of a rotatable member 648 of a motion conversion mechanism 622. The insertion mechanism 600 also differs from the fourth exemplary insertion mechanism 300 by including a hollow delivery needle 606, a cannula 610, and a cannula guide 614 for fluid delivery. Other elements of the fifth exemplary insertion mechanism 600 in FIGS. 14-16 which are similar to the elements of the fourth exemplary insertion mechanism 300 are designated by the same reference numeral, incremented by 300. A description of many of these elements is abbreviated or even eliminated in the interest of brevity. Further, the insertion mechanism 600 may be incorporated into a drug delivery device such as the drug delivery device 10 depicted in FIG. 1 or the drug delivery device 11 depicted in FIG. 12.

The insertion mechanism 600 provides a cannula guide 614 and a hub 616 that are removably attached so that they may disconnect when the hub 616 moves in the proximal direction D to retract the hollow delivery needle 606. In FIG. 14, the motion conversion mechanism 622 is shown in a pre-loaded configuration, and a rotatable member 648 is rotated in a direction G to load the cannula 610. A stop block 651 is configured to move within a semi-circular groove (not illustrated) formed in the housing 602, and slides relative to a surface of the rotatable member 648. The stop block 651 is in a first position in FIG. 14 such that a trailing end 631 is abutting against an internal wall of the housing 602 so that the stop block 651 cannot rotate further in the G direction. As such, when the insertion mechanism 600 is being loaded and the rotatable member 648 is rotated in the G direction, a leading end 633 of the stop block 651 abuts against a trailing edge 635 of the rotatable member 648 to stop the rotatable member 648 from further rotating in the G direction. In the loaded configuration shown in FIG. 15, a trigger (not illustrated, but similar to the trigger 500 of FIGS. 8 and 9) holds a corner 804 of the rotatable member 538 prior to activation. In this configuration, the trailing edge 635 of the rotatable member is spaced away from the leading end 633 of the stop block 651.

When the trigger releases the rotatable member 648, the rotatable member 648 rotates in the H direction and moves relatively to the stop block 651 until a leading edge 637 of the rotatable member 648 contacts a trailing end 631 of the stop block 661. When the leading edge 637 contacts the stop block 651, the rotatable member 648 carries the stop block 651 in rotation in the H direction until a protruding portion of the leading end 633 of the stop block 651 contacts an internal wall (not illustrated) of the housing 602, preventing the rotatable member 648 from further rotating in the H direction. The internal walls of housing, which define the travel path of the stop block 651, are sized to engage with the protruding portion of the stop block 651, but do not engage with the rotatable member 648 as the rotatable member 648 rotates. In FIG. 16, the rotatable member 648 has completed a 360 degree rotation in the H direction, or has completed first and second strokes without pausing between the first and second strokes. At the end of the second stroke, the protruding portion of the leading end 633 of the stop block 651 and the internal wall of the housing 602 are engaged to prevent the rotatable member 648 from rotating further in the H direction.

The motion conversion mechanism 622 may convert rotational motion of the rotatable member 648 to linear motion of the hub 616 and cannula guide 614 via a scotch yoke mechanism. While not illustrated, the rotatable member 648 may include a pin or other coupling member that engages in a slot 686 of a yoke 652 in a similar manner as the scotch yoke mechanism of the motion conversion mechanism 322 of FIGS. 8 and 9. In contrast to the motion conversion mechanism 322 of FIGS. 8 and 9, the motion conversion mechanism 622 of the insertion mechanism 600 of FIGS. 14-16 permits the rotatable member 648 to complete at least a full 360 degree rotation, i.e. first and second strokes, to insert the cannula 610 and hollow delivery needle 606 into the patient and retract the hollow delivery needle 606 back to its second hub position. During the first stroke of approximately a 180 degree rotation, the hub 616 and the cannula guide 614 move together as a unit in the distal direction E to insert the hollow needle (not illustrated) and the cannula 610 into a patient. At a midpoint of the rotation, i.e. at the end of the first stroke, the hub 616 is in the second hub position and the cannula guide 614 is in the second cannula guide position (not shown). Without the rotatable member 648 pausing, the hub 616 and cannula guide 614 separate so that the cannula guide 614 remains in the second cannula guide position while the hub 616 continues in the proximal direction D to return to the first hub position. This example allows for a more compact design, and may be configured to operate with cannulas 610 and hollow needles 606 of many different lengths. The distance the cannula 610 and hollow needle 606 can travel into a patient may be governed by the diameter of a drum of the rotatable member 648 and the position of the pin.

Figure 17:
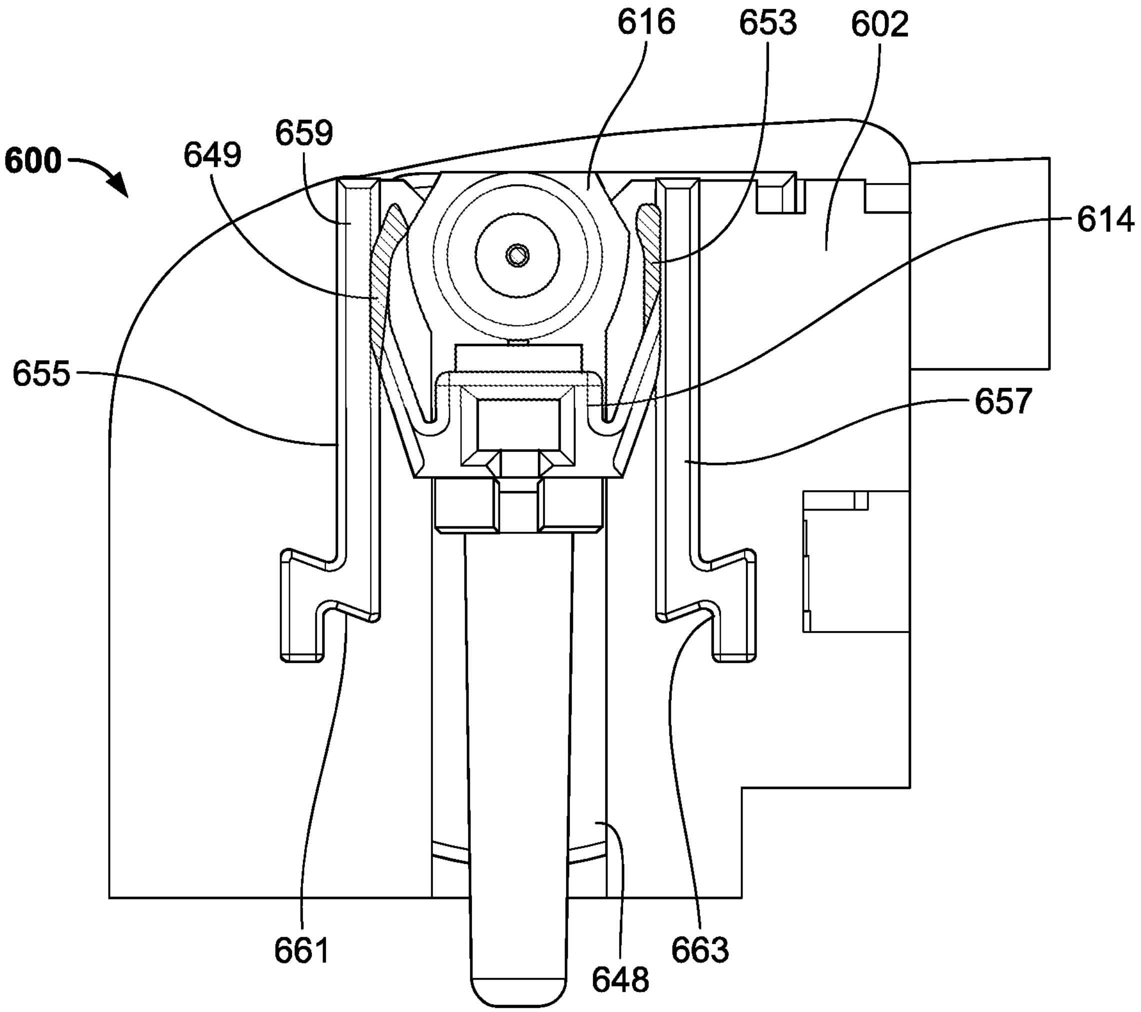
FIG. 17 illustrates a hub and cannula guide of the insertion mechanism of FIGS. 14-16.

In FIG. 17, the cannula guide 614 and the hub 616 are in the pre-fired configuration. In this example, the cannula guide 614 includes first and second deformable arms 649, 651 that are guided by first and second sides 655, 657 of a track 659 formed in the housing 602. As the cannula guide 614 moves from the first cannula guide position to the second cannula guide position, the deformable arms 649, 653 slide against the first and second sides 655, 657 of the track 659, respectively, which cause each arm 649, 653 to bend inwardly as the cannula guide 614 moves in the distal direction E. At or before the point of cannula insertion, the deformable arms 649, 653 flex outwardly at a bend 661, 663 in each side 655, 657 of the track 659. Each bend 661, 663 engages the arm 649, 653 of the cannula guide 614 to prevent the cannula guide 614 from moving in the proximal direction D when the hub 616 returns to the initial hub position. In this example, the track 659 protrudes outwardly from a flat surface of the housing 602, however in other examples, the track 659 may be a groove that receives a portion of each arm 649, 653 of the cannula guide 614.

When the hub 616 returns to the first hub position, the hollow needle 606 is in position to deliver the drug to the cannula 610 which remains inserted in the patient. The insertion mechanism 600 may deliver drug to a patient in the same or similar manner as described and illustrated above with reference to FIG. 13.

Described below is an embodiment of a method of operating a drug delivery device, such as the drug delivery device illustrated in FIG. 1 and the drug delivery device 11 of FIG. 12, incorporating the insertion mechanism 100, 101, 19, 300, and 600 shown in FIGS. 2-7, 10 and 11, 12 and 13, 8 and 9, and 14-17. The method may begin with providing a patient or a healthcare provider (e.g., a caregiver, nurse, doctor, etc.) with the wearable drug delivery device 10, 11. Next, the patient or healthcare provider may dispose the bottom wall 36, 37 of the drug delivery device 10, 11 in contact with the patient's tissue 12 to adhere or otherwise temporarily attach the bottom wall 36, 37 of the drug delivery device 10, 11 to the patient's skin 12. To activate the insertion mechanism 100, 101, 19, 300, and 600, the patient or healthcare provider may depress the actuator 28, which in turn may displace the activation member 170 such that the activation member 170 disengages or releases the power source 118. As a result, the torsion spring 134 of the power source 118 is released, providing rotational motion to the motion conversion mechanism 122, 123, 21, 322, and 622. The rotational motion is converted by the motion conversion mechanism 122, 123, 21, 322, and 622 to linearly move the hub 116, 117, 119, 316, and 616 the trocar 106 or hollow delivery needle 105, 107, 306, 606 and the manifold 114 or cannula guide 113, 115, 614 in a distal direction E so that the trocar 106 or hollow delivery needle 105, 107, 306, 606 penetrates the patient's skin.

The method may include activating the motion conversion mechanism 122, 123, 21, 322, and 622 by rotating the rotating member 148, 149, 348, and 648 operatively coupled to the power source. By rotating the rotating member 148, 149, 348, and 648 in the rotational direction C or H, the pin 150 and 350 slidably received in the slot 186, 386, and 686 formed in the yoke 152, 153, 352, and 652 rotates over the first arc 216 and 416 or 180 degrees causing the yoke 152 and 352 to move linearly in the distal direction E. Continued rotation of the rotatable member 148, 149, 348, and 648 in the rotational direction C rotates the pin 150 and 350 over the second arc 218 and 418 or another 180 degrees causing the yoke 152, 153, 352, and 652 to move linearly in the proximal direction D and retract the trocar 106 or hollow delivery needle 105, 107, 306, 606.

In another embodiment, the hollow delivery needle 306 may remain in the patient and the hub 316 and manifold 314 may remain at the distal end of the housing 302 until fluid delivery is completed. Subsequent to or concurrently with insertion of the hollow delivery needle 306, the method may include: (a) activating the container access mechanism 29 to insert the container needle 31 through the septum 32 to establish fluid communication between the container 14 and the sterile fluid flow path 18 of the fluid connector 22; and (b) activating the drive mechanism 24 to expel the drug 46 from the container 14 through the fluid pathway connector 22, and into the hollow delivery 306 for delivery to the patient.

In a different embodiment, the hollow cannula 110 may also be inserted into the patient's tissue 12 to introduce delivery path. Subsequently, the hub 116 may be disconnected from the manifold 114 to retain the cannula 110 inserted in the patient's tissue 12 and the trocar 106 may be retracted from the patient by moving the hub 116 in the proximal direction D. Subsequent to, or concurrently with, insertion of the cannula 110, the method may include: (a) activating the container access mechanism 29 to insert the container needle 31 through the septum 32 to establish fluid communication between the container 14 and the sterile fluid flow path 18 of the fluid connector 22; and (b) activating the drive mechanism 24 to expel the drug 46 from the container 14 through the fluid pathway connector 22, and into the cannula 110 for delivery to the patient. In some embodiments, activating the insertion mechanism 54, the container access mechanism 29, and/or the drive mechanism 24 may be accomplished through a single depression of the actuator 28. To disconnect the hub 116 and the manifold 114, the catch member 138 engages the proximally facing surface 214 of the manifold 114, retaining the manifold 114 in the second manifold position while the hub 116 returns to the first hub position 116.

In yet another example, the hollow cannula 109, 111, and 610 may remain in the patient, the cannula guide 113, 115, 614 may remain at the distal end of the housing, and the hub 117, 119, and 616 and hollow delivery needle 105, 107, 306, 606 may return to the first hub position. In this position, the hollow delivery needle 105, 107, 306, 606 is in fluid connection with the cannula 109, 111, 610. The method may include (a) activating the container access mechanism to insert the container needle through the septum to establish fluid communication between the container and the sterile fluid flow path 19 of the fluid connector 23; and (b) activating the drive mechanism 25 to expel the drug from the container through the fluid pathway connector 23, and into the cannula 109, 111, 610 for delivery to the patient.

The method may include engaging the rotatable member 148, 149 and 348 with an obstructing edge 194 and 494 to prevent the rotatable 148, 149, and 348 member from rotating. In one case, engaging the rotatable member 148, 149, and 348 includes rotating the spring-biased lock member 500 having the obstructing edge 494 towards the rotatable member 148, 149, and 348 to engage with the non-circular portion 160 and 360 of the rotatable member 148, 149, and 348. In another embodiment, the housing 102 may include the obstructing edge 194 and 494 configured to engage with the non-circular portion 160 and 360 of the rotatable member 148 and 348 and stop the rotatable member 148, 149, and 348 from continual rotation. In another example, the rotatable member 648 may be activated and may engage with the stop block 651 to stop the rotatable member 648 from continual rotation.

The methods and mechanisms described herein provide advantages over known insertion devices, such as simpler design, increased reliability, decrease in patient discomfort and anxiety, increase in accuracy, and decrease in terms of costs and time of manufacturing. Furthermore, the insertion mechanisms 100, 101, 19, 300, and 600 of the present disclosure may be easily adapted for use with many different wearable drug delivery devices and may be customized for specific patient populations. The insertion mechanisms 100, 101, 19, 300, and 600 may be implemented in a wide variety of wearable drug delivery devices configured with various drive mechanisms, having various forms and sizes, and including various drugs. The operation of the insertion mechanisms 100, 101, 19, 300, and 600, and particularly the power sources 118 and the motion conversion mechanism 122, 123, 21, 322, and 622 are not limited in operation or function by the drive mechanism 24, 25, the activation mechanism 170 or 270 or the form of the drug delivery device 10, 11. Further, the insertion mechanisms 100, 101, 19, 300, and 600 may be adapted or customized to minimize pain for specific patients and patient populations. For example, the travel distance between the pre-fired configuration and the inserted configuration of the manifolds 114 and 314, cannula guides 113, 115, 614, and the hubs 116, 117, 119, 316 may be minimized. The mass of the manifolds 114 and 314 and cannula guides 113, 115, 614 may be decreased to lessen the insertion impact force imparted onto the patient.

The insertion mechanisms 100, 101, 19, 300, and 600 may also increase patient comfort and decrease potential patient anxiety. For example, the insertion mechanism 100 may automatically operate and the hub 116 may be configured to immediately retract the trocar 106 upon insertion of the cannula 110 in the patient, minimizing time the trocar 106 is disposed in the patient's body. In conventional methods and mechanisms, patients may be required to insert the trocar or rigid needle into themselves as they advance a button into the device. This type of insertion mechanism may be a cause of anxiety or intimidation to the patient because they are controlling the insertion of the trocar with the advancement of the button. Additionally, known methods and mechanisms include rigid needles combined with an external safety guard that may remain in the patient's skin when the patient is removing the wearable device. In contrast, the disclosed wearable drug delivery device may have a smaller injection site and can be configured to retract the trocar 106 or hollow delivery needle 306 before the patient removes the wearable device.

The motion conversion mechanism 322 of the insertion mechanism 300 of FIGS. 8 and 9 and the motion conversion mechanism 622 beneficially provides a simpler operation with fewer moving parts, a reduced number of components, and a compact design. For example, the insertion mechanism 300 requires fewer parts as the housing 302 is simpler, the hub 316, manifold 314, and yoke 352 form a unified component, and the insertion mechanism 300 does not require a cannula. With fewer components and a simpler design, the provided insertion mechanism 300 may have reduced manufacturing and assembly costs. However, the scope of the present disclosure is not limited to these or any other benefits and advantages described herein, and other benefits and advantages may result from the disclosed embodiments and any modifications thereto in accordance with principles of the present disclosure.

Drug Information

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit®) (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858) as well as erythropoietin molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4;

Myostatin binding proteins, peptibodies, and related proteins, and the like, including myostatin specific peptibodies, particularly those described in U.S. Publication No. 2004/0181033 and PCT Publication No. WO 2004/058988, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1;

Interleukin 1-receptor 1 ("IL1-R1") specific antibodies, peptibodies, and related proteins, and the like, including but not limited to those described in U.S. Publication No. 2004/097712, in parts pertinent to IL1-R1 specific binding proteins, monoclonal antibodies in particular, especially, without limitation, those designated therein: 15CA, 26F5, 27F2, 24E12, and 10H7, as disclosed in the aforementioned publication;

Ang2 specific antibodies, peptibodies, and related proteins, and the like, including but not limited to those described in PCT Publication No. WO 03/057134 and U.S. Publication No. 2003/0229023, particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4(N), Con4(N) 1K WT, 2xCon4(N) 1K; L1C; L1C 1K; 2xL1C; Con4C; Con4C 1K; 2xCon4C 1K; Con4-L1(N); Con4-L1C; TN-12-9(N); C17 (N); TN8-8(N); TN8-14(N); Con 1(N), also including anti-Ang 2 antibodies and formulations such as those described in PCT Publication No. WO 2003/030833, particularly Ab526; Ab528; Ab531; Ab533; Ab535; Ab536; Ab537; Ab540; Ab543; Ab544; Ab545; Ab546; A551; Ab553;

Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, as disclosed in the foregoing publication;

NGF specific antibodies, peptibodies, and related proteins, and the like including, in particular, but not limited to those described in U.S. Publication No. 2005/0074821 and U.S. Pat. No. 6,919,426, particularly as to NGF-specific antibodies and related proteins in this regard, including in particular, but not limited to, the NGF-specific antibodies therein designated 4D4, 4G6, 6H9, 7H2, 14D10 and 14D11, as disclosed in the foregoing publication;

CD22 specific antibodies, peptibodies, and related proteins, and the like, such as those described in U.S. Pat. No. 5,789,554, as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63: 5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, including but not limited to antibodies designated therein as follow: 16H (having light chain variable and heavy chain variable sequences SEQ ID NO: 1 and SEQ ID NO:7 respectively therein); 5D (having light chain variable and heavy chain variable sequences SEQ ID NO: 2 and SEQ ID NO:9 respectively therein); 2H (having light chain variable and heavy chain variable sequences SEQ ID NO:3 and SEQ ID NO: 10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO: 13 respectively therein); and 15H (having light chain variable and heavy chain variable sequences SEQ ID NO:4 and SEQ ID NO: 12 respectively therein);

IL-15 specific antibodies, peptibodies, and related proteins, and the like, such as, in particular, humanized monoclonal antibodies, particularly antibodies such as those disclosed in U.S. Publication Nos. 2003/0138421; 2003/

023586; and 2004/0071702; and U.S. Pat. No. 7,153,507, as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, as disclosed in the foregoing publication and in Thakur et al. (1999), Mol. Immunol. 36:1107-1115. Specific antibodies include those having the heavy chain of SEQ ID NO: 17 and the light chain of SEQ ID NO: 18; those having the heavy chain variable region of SEQ ID NO:6 and the light chain variable region of SEQ ID NO:8; those having the heavy chain of SEQ ID NO: 19 and the light chain of SEQ ID NO:20; those having the heavy chain variable region of SEQ ID NO: 10 and the light chain variable region of SEQ ID NO: 12; those having the heavy chain of SEQ ID NO:32 and the light chain of SEQ ID NO:20; those having the heavy chain variable region of SEQ ID NO:30 and the light chain variable region of SEQ ID NO: 12; those having the heavy chain sequence of SEQ ID NO:21 and the light chain sequence of SEQ ID NO:22; those having the heavy chain variable region of SEQ ID NO: 14 and the light chain variable region of SEQ ID NO: 16; those having the heavy chain of SEQ ID NO:21 and the light chain of SEQ ID NO:33; and those having the heavy chain variable region of SEQ ID NO: 14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO: 17 as disclosed therein and having a complete light chain of SEQ ID NO: 18 as disclosed therein;

TALL-1 specific antibodies, peptibodies, and the related proteins, and the like, and other TALL specific binding proteins, such as those described in U.S. Publication Nos. 2003/0195156 and 2006/0135431, as to TALL-1 binding proteins, particularly the molecules of Tables 4 and 5B, as disclosed in the foregoing publications;

Parathyroid hormone ("PTH") specific antibodies, peptibodies, and related proteins, and the like, such as those described in U.S. Pat. No. 6,756,480, particularly in parts pertinent to proteins that bind PTH;

Thrombopoietin receptor ("TPO-R") specific antibodies, peptibodies, and related proteins, and the like, such as those described in U.S. Pat. No. 6,835,809, particularly in parts pertinent to proteins that bind TPO-R;

Hepatocyte growth factor ("HGF") specific antibodies, peptibodies, and related proteins, and the like, including those that target the HGF/SF: cMet axis (HGF/SF: c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, particularly in parts pertinent to proteins that bind HGF;

TRAIL-R2 specific antibodies, peptibodies, related proteins and the like, such as those described in U.S. Pat. No. 7,521,048, particularly in parts pertinent to proteins that bind TRAIL-R2;

Activin A specific antibodies, peptibodies, related proteins, and the like, including but not limited to those described in U.S. Publication No. 2009/0234106, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, particularly in parts pertinent to proteins that bind TGF-beta;

Amyloid-beta protein specific antibodies, peptibodies, related proteins, and the like, including but not limited to those described in PCT Publication No. WO 2006/081171, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/

IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-a531 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGB mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19: 5138-5143); G207, 1716; NV1020; NV12023; NV1034 and NV1042 (Vargehes et al. (2002), Cancer Gene Ther., 9 (12): 967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery device, insertion mechanisms, drive mechanisms, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the device, drive mechanisms, systems, methods, and their elements.

What is claimed:

1. A wearable drug delivery device comprising:

a housing;

a container positioned at least partially within the housing;

an insertion mechanism positioned at least partially within the housing and comprising:

a delivery member connected or configured to be connected in fluid communication with the container, the delivery member being moveable between a first position wherein an insertion portion of the delivery member is positioned within the housing and a second position wherein the insertion portion of the delivery member is positioned exterior to the housing for insertion into a patient, a hub operably coupled with the delivery member, a power source configured to generate rotational motion, and a motion conversion mechanism operably coupled with the power source and the hub, the motion conversion mechanism comprising a slot configured to convert the rotational motion of the power source into linear motion of the hub to move the delivery member between the first position and the second position, wherein operation of the power source causes at least a portion of the motion conversion mechanism comprising the slot to move with respect to the housing.

2. The wearable drug delivery device of claim 1, comprising at least one fluid conduit configured to fluidly connect the delivery member and the container, the at least one fluid conduit being coupled to the hub such that at least a portion of the fluid conduit and the hub translate jointly during insertion of the delivery member into the patient.

3. The wearable drug delivery device of claim 1, wherein the delivery member comprises a hollow needle.

4. The wearable drug delivery device of claim 1, wherein the delivery member comprises a solid trocar.

5. The wearable drug delivery device of claim 1, wherein, the hub, in moving from the first position to the second position, moves with respect to a rotational axis of the motion conversion mechanism.

6. The wearable drug delivery device of claim 1, comprising an adhesive applied to an exterior wall of the housing for attaching the housing to skin of a patient.

7. The wearable drug delivery device of claim 6, comprising an opening formed in the exterior wall of the housing, wherein the insertion portion of the delivery member extends through the opening in the second position.

8. The wearable drug delivery device of claim 1, wherein the at least a portion of the motion conversion mechanism comprises a rotatable member operably coupled to the hub and rotatable about a rotational axis by the power source.

9. The wearable drug delivery device of claim 8, wherein the rotational axis is traverse to a longitudinal axis of the delivery member.

10. The wearable drug delivery device of claim 8, wherein initial rotation of the rotatable member causes the delivery member to translate from the first position to the second position and subsequent rotation of the rotatable member causes the delivery member to translate from the second position to the first position.

11. The wearable drug delivery device of claim 8, wherein the motion conversion mechanism comprises a pin slidably received in the slot, wherein rotation of the rotatable member causes the pin to slide along a surface defining the slot.

12. The wearable drug delivery device of claim 11, wherein the pin is fixed to the rotatable member.

13. The wearable drug delivery device of claim 8, wherein the power source comprises a torsion spring.

14. The wearable drug delivery device of claim 13, wherein at least a portion of the torsion spring is exterior to the rotatable member.

15. The wearable drug delivery device of claim 8, wherein the rotational axis is stationary or substantially with respect to the housing during operation of the power source.

16. The wearable drug delivery device of claim 1, wherein the motion conversion mechanism comprises a projection slidably received in the slot, and wherein at least a portion of the projection is aligned with at least a portion of the hub when viewed along a rotational axis of the power source.

17. The wearable drug delivery device of claim 1, wherein the motion conversion mechanism comprises a projection slidably received in the slot, wherein the projection is directly coupled with the hub.

18. The wearable drug delivery device of claim 1, wherein the motion conversion mechanism comprises a projection slidably received in the slot, wherein, in at least one position of the projection, a longitudinal axis of the projection crosses through a longitudinal axis of the delivery member.

* * * * *